US011674148B2

(12) United States Patent
Kim et al.

(10) Patent No.: US 11,674,148 B2
(45) Date of Patent: Jun. 13, 2023

(54) **OSNF-YA5 GENE FROM *ORYZA SATIVA* FOR INCREASING NITROGEN AVAILABILITY OF PLANT AND USES THEREOF**

(71) Applicant: SEOUL NATIONAL UNIVERSITY R&DB FOUNDATION, Seoul (KR)

(72) Inventors: Ju-Kon Kim, Gangwon-do (KR); Jun Sung Seo, Gangwon-do (KR); Jae Sung Shim, Gwangju (KR); Sung Hwan Kim, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 25 days.

(21) Appl. No.: 17/392,841

(22) Filed: Aug. 3, 2021

(65) Prior Publication Data

US 2023/0055096 A1 Feb. 23, 2023

(51) Int. Cl.
*C12N 15/82* (2006.01)
*A01H 4/00* (2006.01)

(52) U.S. Cl.
CPC ......... *C12N 15/8262* (2013.01); *A01H 4/008* (2013.01)

(58) Field of Classification Search
CPC .............................. C12N 15/8262; A01H 4/008
See application file for complete search history.

(56) References Cited

U.S. PATENT DOCUMENTS

| | | | |
|---|---|---|---|
| 4,940,838 A | 7/1990 | Schilperoort et al. | |
| 9,447,426 B2 * | 9/2016 | Matsunaga | C12N 15/8273 |
| 2017/0058288 A1 * | 3/2017 | Kim | C07K 14/415 |

FOREIGN PATENT DOCUMENTS

| | | | | |
|---|---|---|---|---|
| EP | 0116718 B1 | 5/1990 | | |
| EP | 0 120 516 B1 | 10/1991 | | |
| KR | 10-1255413 B1 | 4/2013 | | |
| KR | 10-2070128 B1 | 1/2020 | | |
| WO | WO-2014188428 A1 * | 11/2014 | ........... | C07K 14/415 |

OTHER PUBLICATIONS

Zhao, M et al., Involvement of miR169 in the nitrogen-starvation responses in *Arabidopsis*, 2011, New Phytologist, 190, 906-915 (Year: 2011).*
Li, W et al., The *Arabidopsis* NFYA5 Transcription Factor Is Regulated Transcriptionally and Posttranscriptionally to Promote Drought Resistance, 2008, The Plant Cell, 20, 2238-2251. (Year: 2008).*
Shin, S et al., Transcriptomic analyses of rice (*Oryza sativa*) genes and non-coding RNAs under nitrogen starvation using multiple omics technologies, 2018, BMCGenomics, 19, 532 (Year: 2018).*
Yang, W et al., Genome-wide identification and co-expression network analysis of the OsNF-Y gene family in rice, 2017, The Crop Journal, 5, 21-31 (Year: 2017).*
Thirumurugan, T et al., Identification, characterization and interaction of HAP family genes in rice, 2008, Molecular Genetics and Genomics, 279, 279-289 (Year: 2008).*
Ee, D et al., The NF-YA transcription factor OsNF-YA7 confers drought stress tolerance of rice in an abscisic acid independent manner, 2015, Plant Science, 241, 199-210 (Year: 2015).*
Congreves, K et al., Nitrogen Use Efficiency Definitions of Today and Tomorrow, 2021, Frontiers in Plant Science, 12. 1-10 (Year: 2021).*
Yu, G et al. Overexpression of miR169o, an Overlapping MicroRNA in Response to Both Nitrogen Limitation and Bacterial Infection, Promotes Nitrogen Use Efficiency and Susceptibility to Bacterial Blight in Rice, 2018, Plant and Cell Physiology, 59(6): 1234-1247. (Year: 2018).*
Wang, W. et al., "NRT1.1s in plants: functions beyond nitrate transport", Journal of Experimental Botany, vol. 71, No. 15 pp. 4373-4379, 2020.
Hu, B. et al., "Variation in NRT1.1B contributes to nitrate-use divergence between rice subspecies", Nature Genetics, vol. 47, pp. 834-838, 2015.
Wang, W. et al., "Expression of the Nitrate Transporter Gene OsNRT1.1A/ OsNPF6.3 Confers High Yield and Early Maturation in Rice", Plant Cell, vol. 30, pp. 638-651, 2018.
Ueda, Y. et al., "Gene regulatory network and its constituent transcription factors that control nitrogen-deficiency responses in rice", New Phytologist, vol. 227, pp. 1434-1452, 2020.
Zhao, H. et al., "The *Arabidopsis thaliana* Nuclear Factor Y Transcription Factors", Front Plant Sci, vol. 7, article 2045, 2016.
Myers, Z. A. & Holt, B. F. "Nuclear Factor-Y: still complex after all these years?", Current Opinion in Plant Biology, vol. 45, pp. 96-102, 2018.
Lee, D. K. et al., "The NF-YA transcription factor OsNF-YA7 confers drought stresstolerance of rice in an abscisic acid independent manner", Plant Science, vol. 241, pp. 199-210, (2015).
Redillas, M. et al., "Allantoin accumulation through overexpression of ureide permease1 improves rice growth under limited nitrogen conditions", Plant Biotechnol Journal, vol. 17, pp. 1289-1301, 2019.
In-Cheol Jang et al., "Subcellular targeting of green fluorescent protein to plastids in transgenic rice plants provides a high-level expression system", Molecular Breeding, vol. 5, pp. 453-461, 1999.
Shim, J. S. et al., "Overexpression of OsNAC14 Improves Drought Tolerance in Rice", Frontiers in Plant Science, vol. 9, article 310, 2018.
Zhongfu Ni et al., "Altered circadian rhythms regulate growth vigour in hybrids and allopolyploids", Nature, vol. 457, pp. 327-331, 2009.
Jung, H., et al., "OsIAA6, a member of the rice Aux/IAA gene family, is involved indrought tolerance and tiller outgrowth", Plant Science, vol. 236, pp. 304-312, (2015).

* cited by examiner

*Primary Examiner* — Anne Kubelik
*Assistant Examiner* — Aleksandar Radosavljevic
(74) *Attorney, Agent, or Firm* — The PL Law Group, PLLC

(57) ABSTRACT

The present invention relates to OsNF-YA5 gene from *Oryza sativa* for increasing nitrogen availability of plant and uses thereof. Since the OsNF-YA5 gene of the present invention can increase or improve nitrogen availability of a plant, it can be advantageously used for developing a plant which enables lesser consumption of nitrogen fertilizer while maintaining the same plant yield, i.e., an environment friendly plant with lower production cost.

3 Claims, 13 Drawing Sheets

Specification includes a Sequence Listing.

a

AGCAGTTCAACGGCATCATCCGG (SEQ ID NO: 52) NT
AGCAGTTCAA-------ATCCGG (SEQ ID NO: 53) *osnf-ya5*
(7 nt deletion)

b

```
                           SEQUENCE LISTING

<160> NUMBER OF SEQ ID NOS: 53

<210> SEQ ID NO 1
<211> LENGTH: 882
<212> TYPE: DNA
<213> ORGANISM: Oryza sativa

<400> SEQUENCE: 1
atggaggaca cccgaatcct gcaaaaccac caccaccaga tcctcgccgc cggccggcag        60
ctgcagcagc gccaccactt cccggcaatg ccgccggagc gacaccacca ccctcctcct       120
ccagctcctg gaagccctgc catgaagttc ccaatcatct caggtgactc tgatcttggc       180
aaagatctga agttccatga gtcctccgcg ccgaccatcg ccgcgtactc gccattgcag       240
gagtaccaag gacactttga gctagccctt ggccactcca tggtttgcac caacttctgc       300
aactctgaac aaagctatgg tgtttactcc ccctatggag ctcaaaccat ggctgggagg       360
atgctgctgc cgccggcgat cgccaccgac gtgggtccga tctacgtcaa cgcgaagcag       420
ttcaacggca tcatccggcg gcggctggcg cgcgccaagg cggagcggga gcaccgggtt       480
tcccggagcc ggaagccgta cctccacgag tcgccaccc gccacgccat cgccgcgcg       540 cggggcagcg gcggccgctt cctcaacacc aagaacgcct cctccgccgc cgccgcggcc       600
gccgacgcgg cgccggtgag ctccggtggc ggcgaccacg gggcgagcaa caagagctcg       660
tcggcgtcgg aggcgacgcg cgtgtacgac gacgacgacg acatgggcgc gggcggcggc       720
ggcgacggcg gcgacttcca ccacgcgatg gtcacctcc gctcgccggc gttcttcccg       780
tcgctggccg cgatgatgga cggcggcggc ggcggcggcg aggggaagtg ggcgaccgcg       840
acgcctcacc atggctgccg cgtcgacctc ctcaaggtgt ga                         882

<210> SEQ ID NO 2
```

<211> LENGTH: 293
<212> TYPE: PRT
<213> ORGANISM: Oryza sativa

<400> SEQUENCE: 2

```
Met Glu Asp Thr Arg Ile Leu Gln Asn His His Gln Ile Leu Ala
1               5                   10                  15

Ala Gly Arg Gln Leu Gln Gln Arg His His Phe Pro Ala Met Pro Pro
            20                  25                  30

Glu Arg His His Pro Pro Pro Ala Pro Gly Ser Pro Ala Met
            35                  40                  45

Lys Phe Pro Ile Ile Ser Gly Asp Ser Asp Leu Gly Lys Asp Leu Lys
    50                  55                  60

Phe His Glu Ser Ser Ala Pro Thr Ile Ala Ala Tyr Ser Pro Leu Gln
65                  70                  75                  80

Glu Tyr Gln Gly His Phe Glu Leu Ala Leu Gly His Ser Met Val Cys
                85                  90                  95

Thr Asn Phe Cys Asn Ser Glu Gln Ser Tyr Gly Val Tyr Ser Pro Tyr
            100                 105                 110

Gly Ala Gln Thr Met Ala Gly Arg Met Leu Leu Pro Pro Ala Ile Ala
        115                 120                 125

Thr Asp Val Gly Pro Ile Tyr Val Asn Ala Lys Gln Phe Asn Gly Ile
    130                 135                 140

Ile Arg Arg Arg Leu Ala Arg Ala Lys Ala Glu Arg Glu His Arg Val
145                 150                 155                 160

Ser Arg Ser Arg Lys Pro Tyr Leu His Glu Ser Arg His Arg His Ala
                165                 170                 175

Met Arg Arg Ala Arg Gly Ser Gly Arg Phe Leu Asn Thr Lys Asn
            180                 185                 190

Ala Ser Ser Ala Ala Ala Ala Asp Ala Ala Pro Val Ser Ser
        195                 200                 205

Gly Gly Gly Asp His Gly Ala Ser Asn Lys Ser Ser Ala Ser Glu
    210                 215                 220

Ala Thr Arg Val Tyr Asp Asp Asp Asp Met Gly Ala Gly Gly
225                 230                 235                 240

Gly Asp Gly Gly Asp Phe His His Ala Met Gly His Leu Arg Ser Pro
                245                 250                 255

Ala Phe Phe Pro Ser Leu Ala Ala Met Met Asp Gly Gly Gly Gly
            260                 265                 270

Gly Glu Gly Lys Trp Ala Thr Ala Thr Pro His His Gly Cys Arg Val
    275                 280                 285

Asp Leu Leu Lys Val
    290
```

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
cgccattgca ggagtaccaa                                              20

<210> SEQ ID NO 4
<211> LENGTH: 20
<212> TYPE: DNA

```
<213> ORGANISM: Artificial Sequence
<220> FEATURE:
<223> OTHER INFORMATION: primer

<400> SEQUENCE: 4
tgcagaagtt ggtgcaaacc                                               20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
ttaagcagct agccgggaat                                               20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gccaagaaca acttgccaat                                               20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
tggtcctgaa gagttgcaga                                               20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
aaggacacag gcaagtcatc                                               20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
gagatggaag agagcaaggc                                               20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
ctctacacaa ggacacaggc                                               20
```

```
<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
gtgactcgag gttggtgcat                                                 20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
tgatgaagcc gtggtgttct                                                 20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
tctacggtga cgatgtgcag                                                 20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
agagacagcc tctcctcgac                                                 20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
atcatcgggg atgtgctgtc                                                 20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
atggccgtga ccagtatgac                                                 20

<210> SEQ ID NO 17
<211> LENGTH: 20
<212> TYPE: DNA
<213> ORGANISM: Artificial Sequence
<220> FEATURE:
```

```
<223> OTHER INFORMATION: primer

<400> SEQUENCE: 17
gcggtgtact acgggatcag                                               20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
gtgtatcggc accgtgaaca                                               20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
tttacccggt tggggattcg                                               20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
cgtcagcgtc ttgatggagt                                               20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
aagaagttcc acgacgtgct                                               20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
gttgaagttt gggagctgcg                                               20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
tgcattggcc aaagttgttc                                               20
```

```
<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
cgctgtcttt ctgactgctg                                        20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
aagcatccgt ggcacttcta                                        20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26 gtcttttcc cctcccctcg                                         20

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
gtcgtgctca gctgcaagta                                        20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
gctgcctctg atttgaccgt                                        20

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
atggagctgc tgctgttcta                                        20

<210> SEQ ID NO 30
<211> LENGTH: 20
<212> TYPE: DNA
<213> ORGANISM: Artificial Sequence
<220> FEATURE:
<223> OTHER INFORMATION: primer
```

```
<400> SEQUENCE: 30
ttcttccatg ctgctctacc                                              20

<210> SEQ ID NO 31
<211> LENGTH: 33
<212> TYPE: DNA
<213> ORGANISM: Artificial Sequence
<220> FEATURE:
<223> OTHER INFORMATION: primer

<400> SEQUENCE: 31
ttgctccgtg gatccatgtc cccctcccgc ccc                               33

<210> SEQ ID NO 32
<211> LENGTH: 43
<212> TYPE: DNA
<213> ORGANISM: Artificial Sequence
<220> FEATURE:
<223> OTHER INFORMATION: primer

<400> SEQUENCE: 32
aaagcggccg caaatcaaga acctgatgaa tttgccatca ctg                    43

<210> SEQ ID NO 33
<211> LENGTH: 39
<212> TYPE: DNA
<213> ORGANISM: Artificial Sequence
<220> FEATURE:
<223> OTHER INFORMATION: primer

<400> SEQUENCE: 33
ttgctccgtg gatccatgga ggacacccga atcctgcaa                         39

<210> SEQ ID NO 34
<211> LENGTH: 36
<212> TYPE: DNA
<213> ORGANISM: Artificial Sequence
<220> FEATURE:
<223> OTHER INFORMATION: primer

<400> SEQUENCE: 34
aaagcggccg caaatcacct tgaggaggtc gacgcg                            36

<210> SEQ ID NO 35
<211> LENGTH: 35
<212> TYPE: DNA
<213> ORGANISM: Artificial Sequence
<220> FEATURE:
<223> OTHER INFORMATION: primer

<400> SEQUENCE: 35
atttgcggcc gctttatggt gagcaagggc gagga                             35

<210> SEQ ID NO 36
<211> LENGTH: 38
<212> TYPE: DNA
<213> ORGANISM: Artificial Sequence
<220> FEATURE:
<223> OTHER INFORMATION: primer

<400> SEQUENCE: 36
ttgaacgatc tgcagttact tgtacagctc gtccatgc                          38

<210> SEQ ID NO 37
<211> LENGTH: 36
```

```
<212> TYPE: DNA
<213> ORGANISM: Artificial Sequence
<220> FEATURE:
<223> OTHER INFORMATION: primer

<400> SEQUENCE: 37
atttgcggcc gctttatggt gagcaagggc gaggag                                36

<210> SEQ ID NO 38
<211> LENGTH: 38
<212> TYPE: DNA
<213> ORGANISM: Artificial Sequence
<220> FEATURE:
<223> OTHER INFORMATION: primer

<400> SEQUENCE: 38
ttgaacgatc tgcagctact tgtacagctc gtccatgc                              38

<210> SEQ ID NO 39
<211> LENGTH: 30
<212> TYPE: DNA
<213> ORGANISM: Artificial Sequence
<220> FEATURE:
<223> OTHER INFORMATION: primer

<400> SEQUENCE: 39
cccaagctta aggaatcttt aaacatacga                                       30

<210> SEQ ID NO 40
<211> LENGTH: 35
<212> TYPE: DNA
<213> ORGANISM: Artificial Sequence
<220> FEATURE:
<223> OTHER INFORMATION: primer

<400> SEQUENCE: 40
tgctctagaa aaacaaaaaa gcaccgactc ggtgc                                 35

<210> SEQ ID NO 41
<211> LENGTH: 40
<212> TYPE: DNA
<213> ORGANISM: Artificial Sequence
<220> FEATURE:
<223> OTHER INFORMATION: primer

<400> SEQUENCE: 41
agcagttcaa cggcatcatc gttttagagc tagaaatagc                            40

<210> SEQ ID NO 42
<211> LENGTH: 37
<212> TYPE: DNA
<213> ORGANISM: Artificial Sequence
<220> FEATURE:
<223> OTHER INFORMATION: primer

<400> SEQUENCE: 42
gatgatgccg ttgaactgct gccacggatc atctgca                               37

<210> SEQ ID NO 43
<211> LENGTH: 43
<212> TYPE: DNA
<213> ORGANISM: Artificial Sequence
<220> FEATURE:
<223> OTHER INFORMATION: primer

<400> SEQUENCE: 43
``` tgttttggc gtcttccatg gcttctctct ctctcttctt ctt          43

<210> SEQ ID NO 44
<211> LENGTH: 41
<212> TYPE: DNA
<213> ORGANISM: Artificial Sequence
<220> FEATURE:
<223> OTHER INFORMATION: primer

<400> SEQUENCE: 44
cgacggccag tgccaagctt tggtgtaggt gtcttatctc a          41

<210> SEQ ID NO 45
<211> LENGTH: 43
<212> TYPE: DNA
<213> ORGANISM: Artificial Sequence
<220> FEATURE:
<223> OTHER INFORMATION: primer

<400> SEQUENCE: 45
cgacggccag tgccaagctt cccaagaata tatctagcat gtc          43

<210> SEQ ID NO 46
<211> LENGTH: 40
<212> TYPE: DNA
<213> ORGANISM: Artificial Sequence
<220> FEATURE:
<223> OTHER INFORMATION: primer

<400> SEQUENCE: 46
cgacggccag tgccaagctt ctcaattcca tctataaccc          40

<210> SEQ ID NO 47
<211> LENGTH: 42
<212> TYPE: DNA
<213> ORGANISM: Artificial Sequence
<220> FEATURE:
<223> OTHER INFORMATION: primer

<400> SEQUENCE: 47
cgacggccag tgccaagctt ggcaaactga taatgggacc ac          42

<210> SEQ ID NO 48
<211> LENGTH: 41
<212> TYPE: DNA
<213> ORGANISM: Artificial Sequence
<220> FEATURE:
<223> OTHER INFORMATION: primer

<400> SEQUENCE: 48
cgacggccag tgccaagctt aagtgaagca gtgagtgccc t          41

<210> SEQ ID NO 49
<211> LENGTH: 42
<212> TYPE: DNA
<213> ORGANISM: Artificial Sequence
<220> FEATURE:
<223> OTHER INFORMATION: primer

<400> SEQUENCE: 49
tccccttgct ccgtggatcc atggaggaca cccgaatcct gc          42

<210> SEQ ID NO 50
<211> LENGTH: 42
<212> TYPE: DNA
<213> ORGANISM: Artificial Sequence

```
<220> FEATURE:
<223> OTHER INFORMATION: primer

<400> SEQUENCE: 50
aatgtttgaa cgatctgcag tcacaccttg aggaggtcga cg          42

<210> SEQ ID NO 51
<211> LENGTH: 21
<212> TYPE: DNA
<213> ORGANISM: Oryza sativa

<400> SEQUENCE: 51
gaagcagttc aaatccggcg g                                 21

<210> SEQ ID NO 52
<211> LENGTH: 23
<212> TYPE: DNA
<213> ORGANISM: Oryza sativa

<400> SEQUENCE: 52
agcagttcaa cggcatcatc cgg                               23

<210> SEQ ID NO 53
<211> LENGTH: 16
<212> TYPE: DNA
<213> ORGANISM: Artificial Sequence
<220> FEATURE:
<223> OTHER INFORMATION: osnfya5 mutant

<400> SEQUENCE: 53
agcagttcaa atccgg                                       16
```

OSNF-YA5 GENE FROM *ORYZA SATIVA* FOR INCREASING NITROGEN AVAILABILITY OF PLANT AND USES THEREOF

GOVERNMENT LICENSE RIGHTS

This invention was made with government support under the New breeding technologies development Program (Project No. PJ01477201 to J.-K.K.), awarded by the Rural Development Administration, Republic of Korea. The government has certain rights in the invention.

BACKGROUND

1. Technical Field

The present invention relates to OsNF-YA5 (*Oryza sativa* Nuclear Factor Y subunit A5) gene from *Oryza sativa* for increasing nitrogen availability of plant and uses thereof.

2. Background Art

Nitrogen (N) is a vital nutrient for plant growth and crop yield improvement. Over the last half-century, global cereal production has double; however, the application amount of N fertilizers has increased by seven times. The excessive use of nitrogen fertilizer led to severe problems in aquatic ecosystems, including eutrophication and groundwater contamination, and contributed to nitrous oxide emissions into the atmosphere, a major cause of climate change. Unfortunately, it was reported that three major cereal crops, rice, wheat, and maize, utilize only 30%-50% of applied N fertilizer for their biomass—the remaining 50%-70% of applied N fertilizer leaked to the environment. Therefore, improving plant N use efficiency (NUE) to reduce the N fertilizer has been a hot research topic in the plant biotechnology field over the last several decades. NUE comprises two major parts, N uptake efficiency (NUpE) and N utilization efficiency (NUtE). So far, intensive studies have been made for the transporters involved in NUpE, especially nitrate transporters (NRT). However, the molecular mechanism of NUtE, which includes N assimilation and remobilization, and N signaling, has been less explored and still largely unknown.

NRT1.1, also named CHL1/NPF6.3, is the first nitrate transporter identified in plants and intensively studied in *Arabidopsis*. NRT1.1 plays an essential role in nitrate uptake and transport as well as acts as a nitrate sensor, called 'transceptor'. In the rice genome, there are three homologs of AtNRT1.1, which are OsNRT1.1A, OsNRT1.1B, and OsNRT1.1C (Wang, W. et al., J. Exp. Bot. (2020) 71:4373-4379). OsNRT1.1B is the functional homolog of AtNRT1.1 and located in the plasma membrane to transport and sense the external nitrate. Single nucleotide variation in OsNRT1.1B gene affected the significant difference in N uptake and signaling between indica and japonica, which suggested that OsNRT1.1 plays a vital role in regulating rice NUE (Hu, B. et al., Nat Genet (2015) 47:834-838). Unlike OsNRT1.1B, OsNRT1.1A is predominantly localized to the tonoplast, although it also has nitrate transporter activity. Overexpression of OsNRT1.1B significantly improves N utilization and yield, while knockout mutant showed severe yield loss compare to control (Wang, W. et al., Plant Cell (2018) 30:638-651). It suggests that OsNRT1.1A also functions as a key regulator in rice NUE although expression pattern and localization are different with those of OsNRT1.1B.

Transcription factors (TFs) involved in the N signaling network have been identified primarily on *Arabidopsis*. ANR1 is first identified MADS-box TF involved in N dependent lateral root (LR) development. LBD37/38 regulate N responsive genes, including NL41/2, NRT1.1, and NRT2.1/2.2/2.5, negatively. TGA1/4 have been identified by the system biology approach and have a global role in N signaling in the roots. ChIP result showed that TGA1/4 could bind to NRT2.1 and NRT2.2 promoters and affects LR initiation. HY5 and HYH, bZIP TFs, involve integrating light and N signaling in plants; moreover, another bZIP TF, bZIP1, transiently binds to the promoters of early responsive genes in N signaling. TCP20 is identified as a regulator of systemic N signaling and induces NRT1.1 expression in N deficient condition. NGT1/HRS1/HHO family TFs have been proven as a regulator in both the N and P signaling pathways. HRS1 and HHO1 have been reported to be the early inducers of nitrate signaling cascades and play a critical role in coordinating N and P response. NLP7 is one of the best-characterized TF in N signaling so far. NLP7 was initially identified as an ortholog to legume NIN protein involving nodulation and NIT protein of *Chlamydomonas*, regulating nitrate reductase (NR) expression. Nitrate triggers NLP7 accumulation in the nuclear and NLP7 activates the expression of key N responsive genes. In rice, orthologs of the above TFs involved in N signaling are also found and response to N starvation. However, only a few of them have been characterized as their physiological functions to date (Ueda, Y. et al., New Phytol (2020) 227:1434-1452).

Nuclear factor Y (NF-Y), also named CCAAT binding factor (CBF) or heme activator protein (HAP), is evolutionarily conserved trimeric TF across the plants, animals, and other eukaryotes. The NF-Y complex comprises the subunits, NF-YA, NF-YB, and NF-YC, and functions in heterodimers or heterotrimers (Zhao, H. et al., Front Plant Sci (2016) 7:2045). Total 36 loci have been annotated NF-Y members (10 NF-YA, 13 NF-YB, and 13 NF-YC) in the *Arabidopsis* genome, and 34 NF-Y members (11 NF-YA, 11 NF-YB, and 12 NF-YC) were annotated in rice genome. So far, the biological function of NF-Y TFs has been identified mainly in the developmental process, including embryo development, seed germination, photomorphogenesis, and flowering time regulation (Zhao, H. et al., 2016). Besides, NF-Y TFs play an important role in abiotic stress responses. AtNF-YAS, AtNF-YB1, and OsNF-YA7 were reported as positive regulators in drought tolerance in *Arabidopsis* and rice. AtNF-YC1 enhanced freezing tolerance, and AtNF-YA1 improved salt tolerance in *Arabidopsis*. NF-YA2-B3-C10 complex activated the expression of HEAT SHOCK FACTOR A3 (HsfA3) under heat stress conditions, which conferred heat stress resistance (Zhao, H. et al., 2016; Myers, Z. A. & Holt, B. F. Curr Opin Plant Biol (2018) 45:96-102; Lee, D. K. et al., Plant Sci (2015) 241:199-210). Recently, different subunits of plant NF-Y have been studied extensively; however, diverse functions of the NF-Y complex still remain limited. Compared to yeast and mammals, plant genome harbors multi-genes of NF-Y subunits and enables more NF-Y complex combinations, indicating that plant NF-Y TFs could involve diverse and intricate regulatory processes.

Meanwhile, 'Transgenic plant having improving nitrogen availability and its manufacturing method' is disclosed in Korean Patent Registration No. 2070128 and 'Plants having enhanced yield-related traits and a method for making the same' is disclosed in Korean Patent Registration No. 1255413. However, OsNF-YA5 gene from *Oryza sativa* for increasing nitrogen availability of plant and uses thereof of the present invention have not been described before.

SUMMARY

The present invention is devised in view of the above-described needs. Inventors of the present invention prepared a transgenic rice plant which overexpresses OsNF-YA5 gene by transformation of a plant cell with recombinant vector which contains a gene encoding OsNF-YA5 protein derived from rice. The inventors found that the transgenic rice plant which overexpresses OsNF-YA5 has considerably better agronomic traits (i.e., plant yield) and higher amino acid content in plant seed compared to the wild type under nitrogen deficient condition. It was also found that the aforementioned effect is obtained based on the direct regulation of expression of OsNRT1.1A (nitrate transporter), which is a gene playing a key role in having enhanced nitrogen utilization, by OsNF-YA5 gene. Based on the findings, it was known that, by enhancing the uptake of nitrogen nutrients from soil and utilization of nitrogen nutrients in plant via the regulation of expression of OsNRT1.1A, the gene encoding OsNF-YA5 protein of rice plays a key role in increasing the nitrogen utilization efficiency of a plant, and the present invention is completed accordingly.

To solve the problems that are described above, the present invention provides a method for increasing nitrogen availability of a plant compared to a non-transgenic plant including transforming a plant cell with a recombinant vector which contains the gene encoding the *Oryza sativa*-derived OsNF-YA5 (*Oryza sativa* Nuclear Factor Y subunit A5) protein to overexpress the gene encoding the OsNF-YA5 protein.

The present invention further provides a method for producing a transformed plant with increased nitrogen availability compared to a non-transgenic plant including transforming a plant cell with a recombinant vector which includes the gene encoding the *Oryza sativa*-derived OsNF-YA5 protein; and regenerating a plant from the transformed plant cell.

The present invention further provides a transformed plant with increased nitrogen availability compared to a non-transgenic plant which is produced by the aforementioned method, and a transformed seed thereof.

The OsNF-YA5 gene of the present invention enhances the nitrogen availability of a plant to induce an improvement of agronomic traits (i.e., plant yield) when compared to the wild type under nitrogen deficient condition. As such, it is expected that the OsNF-YA5 gene of the present invention can be advantageously used for developing a plant which enables lesser consumption of nitrogen fertilizer while maintaining the same plant yield, i.e., an environment friendly plant with lower production cost.

DETAILED DESCRIPTION

Figure 1:
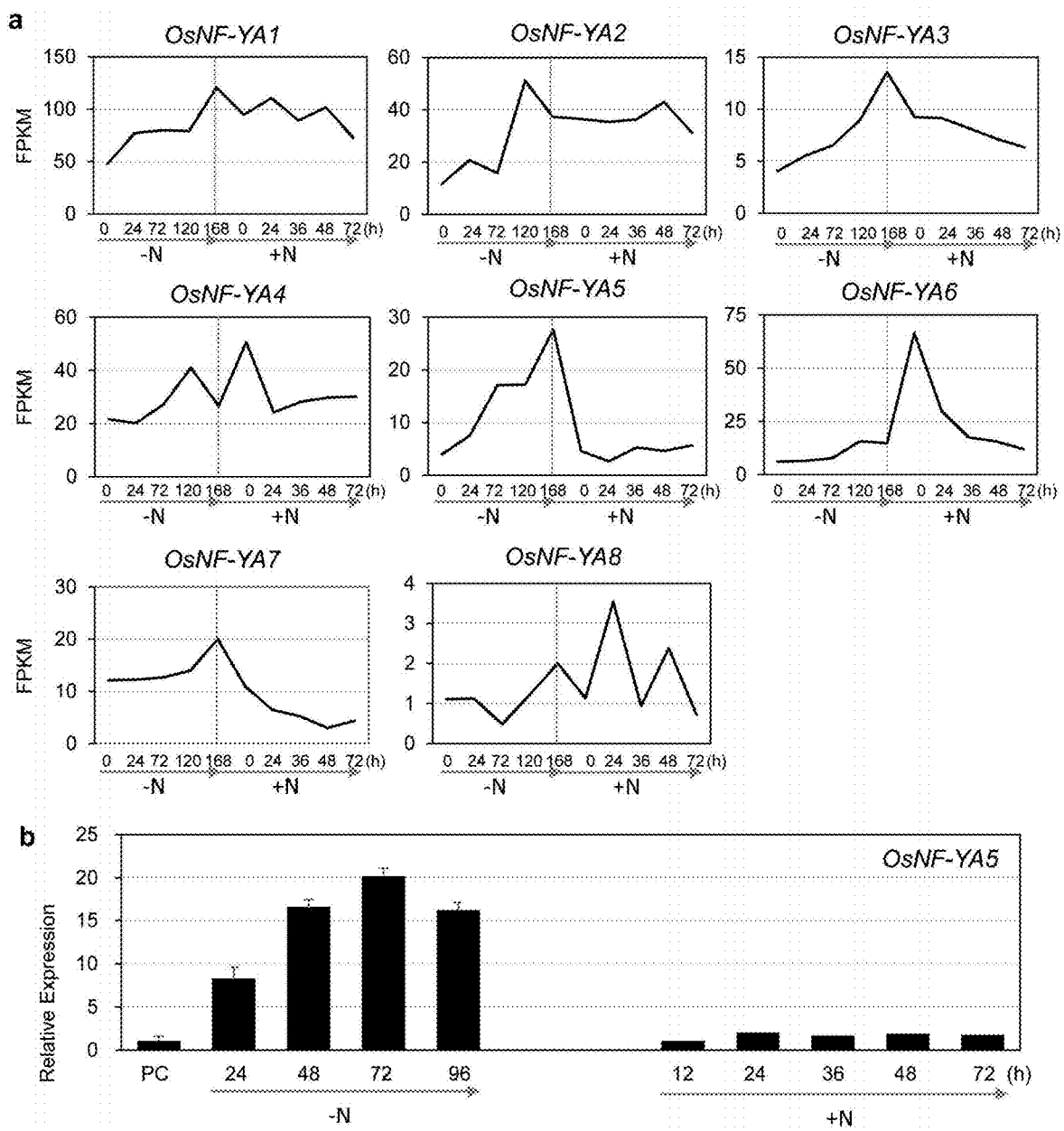
FIG. 1 shows the expression of OsNF-YAs under N modified condition (a) Gene expression pattern of rice NF-YAs under N deficient condition for 7 days and under N replenished condition for 3 days. The expression value is FPKM in previous RNA-seq data35 (b) OsNF-YA5 expression under N deficient condition for 4 days and under N replenished condition for 3 days. The expression level was confirmed by qPCR analysis in the root tissue. Transcript levels were normalized to OsUbi1 expression. Values are the means±standard deviation (SD) of three biological samples (n=3).

To achieve the object of the present invention, the present invention provides a method for increasing nitrogen availability of a plant compared to a non-transgenic plant including transforming a plant cell with a recombinant vector which contains the gene encoding the *Oryza sativa*-derived OsNF-YA5 (*Oryza sativa* Nuclear Factor Y subunit A5) protein to overexpress the gene encoding the OsNF-YA5 protein.

Included in the scope of the OsNF-YA5 protein of the present invention are a protein having the amino acid sequence represented by SEQ ID NO: 2, and functional equivalents of the protein. The term "functional equivalents" indicates a protein having, as a result of addition, substitution, or deletion of an amino acid, at least 70%, preferably at least 80%, more preferably at least 90%, and even more preferably at least 95% sequence homology with the amino acid sequence represented by SEQ ID NO: 2, and it indicates a protein exhibiting substantially the same activity as the protein represented by SEQ ID NO: 2. The expression "substantially the same activity" means the activity for increasing nitrogen availability of a plant compared to a non-transgenic plant.

Also included in the present invention are fragments, derivatives, and analogues of the OsNF-YA5 protein. The terms "fragments", "derivatives", and "analogues" that are described in the present specification indicate a polypeptide with the substantially same biological function or activity as the OsNF-YA5 protein of the present invention.

The present invention also provides the gene encoding the OsNF-YA5 protein of the present invention. Genomic DNA, cDNA, and synthetic DNA encoding the OsNF-YA5 protein are all within the scope of the gene. Preferably, the gene encoding the OsNF-YA5 protein of the present invention may include the nucleotide sequence of SEQ ID NO: 1. Furthermore, homologues of the nucleotide sequence are also within the scope of the present invention. Specifically, the above described gene may comprise a nucleotide sequence which has preferably at least 70%, more preferably at least 80%, still more preferably at least 90%, and most preferably at least 95% homology with the nucleotide sequence of SEQ ID NO: 1. The "sequence homology %" for a certain polynucleotide is identified by comparing a comparative region with two sequences that are optimally aligned. In this regard, a part of the polynucleotide in comparative region may comprise an addition or a deletion (i.e., a gap) compared to a reference sequence (without any addition or deletion) relative to the optimized alignment of the two sequences.

The method for increasing nitrogen availability of a plant according to one embodiment of the present invention is to increase nitrogen availability of a plant compared to a non-transgenic plant by overexpressing the gene encoding the OsNF-YA5 protein, in particular, to increase a plant yield and to increase an amino acid content in a seed compared to a non-transgenic plant under nitrogen deficient condition, but it is not limited thereto. The increase of the plant yield can be an increase of plant height, culm length, total seed number, filling rate or total seed weight, but it is not limited thereto.

The expression "overexpress a gene" means that the gene is overexpressed to the level that is higher than the expression level in a wildtype plant. As a method for introducing the gene into a genome, there is a method for transforming a plant by using an expression vector, in which the gene under regulation of a promoter is included.

In the present specification, the term "recombinant" indicates a cell which replicates a heterogeneous nucleotide or expresses said nucleotide, or a peptide, a heterogeneous peptide, or a protein encoded by a heterogeneous nucleotide. Recombinant cell can express a gene or a gene fragment in the form of a sense or antisense, which are not found in natural state of cell. In addition, a recombinant cell can express a gene that is found in natural state, provided that said gene is modified and re-introduced into the cell by an artificial means.

The term "vector" is used herein to refer DNA fragment (s) and nucleotide molecules that are delivered to a cell. Vector can replicate DNA and be independently reproduced in a host cell. The terms "delivery system" and "vector" are often interchangeably used.

The vector of the present invention can be constructed as a vector which is typically used for cloning or expression. In addition, the vector of the present invention can be constructed by having a prokaryotic cell or an eukaryotic cell as a host. For example, when the vector of the present invention is an expression vector and a prokaryotic cell is employed as a host, a strong promoter for the initiation of transcription (e.g., pLλ promoter, trp promoter, lac promoter, T7 promoter, tac promoter and the like), and a ribosome binding site for the initiation of translation and a termination sequence for transcription/translation are generally comprised. When E. coli is employed as a host cell, a promoter and an operator region relating to the biosynthetic pathway of tryptophan in E. coli, and left-side promoter of phage λ (i.e., pLλ promoter) can be used as a regulation site.

For the recombinant vector according to the present invention, the promoter may be any of CaMV 35S promoter, actin promoter, ubiquitin promoter, pEMU promoter, MAS promoter, and histone promoter, but not limited thereto.

In the present specification, the term "promoter" means a DNA molecule to which RNA polymerase binds in order to initiate its transcription, and it corresponds to a DNA region upstream of a structural gene. The term "plant promoter" indicates a promoter which can initiate transcription in a plant cell. The term "constitutive promoter" indicates a promoter which is active in most of environmental conditions and development states or cell differentiation states. Since a transformant can be selected with various mechanisms at various stages, the constitutive promoter can be preferable for the present invention. Therefore, a possibility for choosing the constitutive promoter is not limited herein.

The recombinant vector of the present invention can be constructed according to a method which is well known to a skilled person in the art. The method includes an in vitro recombinant DNA technique, a DNA synthesis technique, and an in vivo recombinant technique. For inducing mRNA synthesis, the DNA sequence can be effectively linked to a suitable promoter present in the expression vector. In addition, the expression vector may comprise a ribosome binding site as a translation initiation site and a transcription terminator.

Preferred example of the recombinant vector of the present invention is Ti-plasmid vector which can transfer a part of itself, i.e., so called T-region, to a plant cell when the vector is present in an appropriate host such as *Agrobacterium tumefaciens*. Other types of Ti-plasmid vector (see, EP 0 116 718 B1) are currently used for transferring a hybrid DNA sequence to protoplasts that can produce a new plant by appropriately inserting a plant cell or hybrid DNA to a genome of a plant. Especially preferred form of Ti-plasmid vector is a so-called binary vector which has been disclosed in EP 0 120 516 B1 and U.S. Pat. No. 4,940,838. Other vector that can be used for introducing the DNA of the present invention to a host plant can be selected from a double-stranded plant virus (e.g., CaMV), a single-stranded virus, and a viral vector which can be originated from Gemini virus, etc., for example a non-complete plant viral vector. Use of said vector can be advantageous especially when a host plant cannot be easily transformed.

The recombinant vector may comprise at least one selective marker. Said selective marker is a nucleotide sequence having a property of being selected by a common chemical method. Examples include all genes that are useful for distinguishing transformed cells from non-transgenic cells. Specific examples thereof include a gene resistant to herbicide such as glyphosate and phosphinotricine, and a gene resistant to antibiotics such as kanamycin, G418, bleomycin, hygromycin, and chloramphenicol, and aadA gene, but not limited thereto.

For the recombinant vector of the present invention, any conventional terminator can be used. Examples include nopaline synthase (NOS), rice α-amylase RAmy 1 A terminator, a phaseolin terminator, a terminator for octopine gene of *Agrobacterium tumefaciens*, rrnB1/B2 of *Escherichia coli* or the like, but are not limited thereto.

Any plant cell can be employed as the "plant cell" that is used for transformation of a plant. The plant cell may be cultured cells, cultured tissues, cultured organs, or whole plant, preferably cultured cells, cultured tissues, or cultured organs, and more preferably cultured cells in any form. The "plant tissue" may be either differentiated or undifferentiated tissues of a plant, and examples thereof include, although not limited thereto, root, stem, leaf, pollen, seed, tumor tissue, and cells in various forms that are used for culture like single cell, protoplast, shoot, and callus tissue. The plant tissue can be either in planta, or in a state of organ culture, tissue culture, or cell culture.

Also provided by the present invention is a method for producing a transformed plant with increased nitrogen availability compared to a non-transgenic plant including:

transforming a plant cell with a recombinant vector including the gene encoding the *Oryza sativa*-derived OsNF-YA5 protein; and regenerating a plant from the transformed plant cell.

With regard to the method for producing a transformed plant with increased nitrogen availability, scope of the OsNF-YA5 protein and OsNF-YA5 gene is as described in the above.

According to the method for producing a transformed plant of one embodiment of the present invention, by increasing the expression of the gene encoding *Oryza sativa*-derived OsNF-YA5 protein in a transformed plant, a transformed plant having increased nitrogen availability compared to a non-transgenic plant can be produced.

Furthermore, the method for the present invention also includes regenerating a transformed plant from the transformed plant cells. Any method well known in the pertinent art may be used as a method for regenerating a transformed plant from the transformed plant cells. The transformed plant should be regenerated to a whole plant. For many various species, techniques for regeneration of a mature plant from culture of callus or protoplast are well known in the pertinent art.

Also provided by the present invention is a transformed plant produced by the above production method which has increased nitrogen availability compared to a non-transgenic plant, and a transformed seed thereof.

As described in the above, for a case in which the expression of a gene encoding the OsNF-YA5 protein consisting of the amino acid sequence of SEQ ID NO: 2 is enhanced, the transformed plant of the present invention is characterized to have increased nitrogen availability, and the transformed plant with increased nitrogen availability has traits of increased yield and increased amino acid content in a seed compared to a non-transgenic plant under nitrogen deficient condition.

In one embodiment of the present invention, the plant can be a monocot plant such as rice, barley, wheat, rye, corn, sugar cane, oat, or onion, or a eudicot plant such as *Arabidopsis thaliana*, potato, eggplant, tobacco, pepper, tomato, burdock, crown daisy, lettuce, balloon flower, spinach, chard, yam, carrot, water parsley, Chinese cabbage, cabbage, *Raphanus sativus* for. raphnistroides MAK, watermelon, oriental melon, cucumber, zucchini, gourd, strawberry, soybean, mung bean, kidney bean, or sweet pea. The plant preferably can be a monocot plant, more preferably can be a rice, however, it is not limited thereto.

Hereinbelow, the present invention is explained in greater detail in view of the Examples. However, it is evident that the following Examples are given only for exemplification of the present invention and by no means the present invention is limited to the following Examples.

Methods and Materials

Plant Growth Conditions

Rice seeds (*Oryza sativa* cv. Dongjin) were sown on a Murashige-Skoog (MS) solid medium and incubated in the dark for 4 days at 28° C. Seedlings were then transferred to a growth chamber with a light and dark cycle of 16 h light/8 h dark with a light intensity of 200 µmol m$^{-2}$ s$^{-1}$ and relative humidity of 70%. Two-week-old seedlings were used for gene expression analysis. To examine N concentration-dependent response of OsNF-YA5 and OsMIR169s, rice seeds were germinated on MS without nitrogen (Caisson Labs) solid media supplemented with various concentrations of $KNO_3$ or $NH_4NO_3$. Seedlings were harvested two-week after germination for RNA extraction. We prepared the liquid culture solution with nutrients composition as described in the previous report (Redillas, M. et al., Plant Biotechnol J. (2019) 17:1289-1301) and N deficient solution was prepared except N source ($NH_4NO_3$).

Plasmids Construction and Rice Transformation

To generate overexpression plants, the coding sequence of OsNF-YA5 (Os07g0158500) transcript was amplified from rice (*Oryza sativa* L. ssp. *japonica* cv. Nipponbare) total RNAs using the Reverse Transcription System (Promega) and PrimeSTAR HS DNA polymerase (TAKARA). The PCR-amplified OsNF-YA5 coding sequence was cloned into rice transformation vector p700 carrying GOS2 promoter for constitutive overexpression or RCc3 promoter for root specific overexpression. For expression of OsNF-YA5 fused with glucocorticoid receptor (GR), OsNF-YA5 coding sequence omitting stop codon and GR coding sequence was cloned into p700 vector through restriction enzyme-mediated ligation. To generate CRISPR/Cas9-mediated mutagenesis on coding sequence of OsNF-YA5, two individual guide RNAs (gRNAs) targeting first exon (29~51) or fourth exon of OsNF-YA5 (416-438) were respectively cloned into the CRISPR/Cas9 expression vector carrying a rice codon-optimized *Streptococcus pyrogenes* Cas9 (rCRISPR/Cas9) through XhoI and BamHI restriction enzyme sites. Primers used for vector construction is listed in Table 1.

TABLE 1

Primer Sequence Information

| | Nucleotide sequence (5' to 3') | |
|---|---|---|
| PCR primers | Forward | Reverse |
| qRT-PCR | | |
| OsNF-YA5 | CGCCATTGCAGGAGTACCAA (SEQ ID NO: 3) | TGCAGAAGTTGGTGCAAACC (SEQ ID NO: 4) |
| OsmiR169a | TTAAGCAGCTAGCCGGGAAT (SEQ ID NO: 5) | GCCAAGAACAACTTGCCAAT (SEQ ID NO: 6) |
| OsmiR169h | TGGTCCTGAAGAGTTGCAGA (SEQ ID NO: 7) | AAGGACACAGGCAAGTCATC (SEQ ID NO: 8) |
| OsmiR169i | GAGATGGAAGAGAGCAAGGC (SEQ ID NO: 9) | CTCTACACAAGGACACAGGC (SEQ ID NO: 10) |
| OsNRT1.1A | GTGACTCGAGGTTGGTGCAT (SEQ ID NO: 11) | TGATGAAGCCGTGGTGTTCT (SEQ ID NO: 12) |
| ATL15I | TCTACGGTGACGATGTGCAG (SEQ ID NO: 13) | AGAGACAGCCTCTCCTCGAC (SEQ ID NO: 14) |
| ATL7 | ATCATCGGGGATGTGCTGTC (SEQ ID NO: 15) | ATGGCCGTGACCAGTATGAC (SEQ ID NO: 16) |
| ProT | GCGGTGTACTACGGGATCAG (SEQ ID NO: 17) | GTGTATCGGCACCGTGAACA (SEQ ID NO: 18) |
| ANT5 | TTTACCCGGTTGGGGATTCG (SEQ ID NO: 19) | CGTCAGCGTCTTGATGGAGT (SEQ ID NO: 20) |
| LHT1 | AAGAAGTTCCACGACGTGCT (SEQ ID NO: 21) | GTTGAAGTTTGGGAGCTGCG (SEQ ID NO: 22) |

TABLE 1-continued

Primer Sequence Information

Nucleotide sequence (5' to 3')

| PCR primers | Forward | Reverse |
|---|---|---|
| NPF8.1 | TGCATTGGCCAAAGTTGTTC (SEQ ID NO: 23) | CGCTGTCTTTCTGACTGCTG (SEQ ID NO: 24) |
| NPF8.5 | AAGCATCCGTGGCACTTCTA (SEQ ID NO: 25) | GTCTTTTTCCCCTCCCCTCG (SEQ ID NO: 26) |
| NPF5.4 | GTCGTGCTCAGCTGCAAGTA (SEQ ID NO: 27) | GCTGCCTCTGATTTGACCGT (SEQ ID NO: 28) |
| OsUbi1-F-q | ATGGAGCTGCTGCTGTTCTA (SEQ ID NO: 29) | TTCTTCCATGCTGCTCTACC (SEQ ID NO: 30) |
| Subcellular localization | | |
| pHBT_infusion_OsNAC14 | TTGCTCCGTGGATCCATGTC CCCCTCCCGCCCC (SEQ ID NO: 31) | AAAGCGGCCGCAAATCAAGAAC CTGATGAATTTGCCATCACTG (SEQ ID NO: 32) |
| pHBT_infusion_OsNF-YA3 | TTGCTCCGTGGATCCATGGA GGACACCCGAATCCTGCAA (SEQ ID NO: 33) | AAAGCGGCCGCAAATCACCTTG AGGAGGTCGACGCG (SEQ ID NO: 34) |
| pHBTinfusion_sGFP_N | ATTTGCGGCCGCTTTATGGT GAGC AAGGGCGAGGA (SEQ ID NO: 35) | TTGAACGATCTGCAGTTACTTGT ACAGCTCGTCCATGC (SEQ ID NO: 36) |
| pHBTinfusion_mCherry_N | ATTTGCGGCCGCTTTATGGT GAGCAAGGGCGAGGAG (SEQ ID NO: 37) | TTGAACGATCTGCAGCTACTTGT ACAGCTCGTCCATGC (SEQ ID NO: 38) |
| CRISPR/Cas9 | | |
| OsU3pro_Hind3_F | CCCAAGCTTAAGGAATCTTT AAACATACGA (SEQ ID NO: 39) | |
| gRNA:Ter (Xba1)_R | | TGCTCTAGAAAAACAAAAAGC ACCGACTCGGTGC (SEQ ID NO: 40) |
| OsU3_NF-YA5_sgRNA_F | AGCAGTTCAACGGCATCATC GTTTTAGAGCTAGAAA TAGC (SEQ ID NO: 41) | |
| OsU3P_NF-YA5_R | | GATGATGCCGTTGAACTGCTGCC ACGGATCATCTGCA (SEQ ID NO: 42) |
| Transactivation assay | | |
| NRT1.1A_Reporter-R(pGBT6) | | TGTTTTTGGCGTCTTCCATGGCT TCTCTCTCTCTCTTCTTCTT (SEQ ID NO: 43) |
| NRT1.1A_Reporter1-F(pGBT6) | CGACGGCCAGTGCCAAGCTT TGGTGTAGGTGTCTTATCTC A (SEQ ID NO: 44) | |
| NRT1.1A_Reporter2-F(pGBT6) | CGACGGCCAGTGCCAAGCTT CCCAAGAATATATCTAGCAT GTC (SEQ ID NO: 45) | |
| NRT1.1A_Reporter3-F(pGBT6) | CGACGGCCAGTGCCAAGCTT CTCAATTCCATCTATAACCC (SEQ ID NO: 46) | |
| NRT1.1A_Reporter4-F(pGBT6) | CGACGGCCAGTGCCAAGCTT GGCAAACTGATAATGGGAC CAC (SEQ ID NO: 47) | |

TABLE 1-continued

Primer Sequence Information

| PCR primers | Nucleotide sequence (5' to 3') | |
| --- | --- | --- |
| | Forward | Reverse |
| NRT1.1A_Reporter5-F(pGBT6) | CGACGGCCAGTGCCAAGCTT AAGTGAAGCAGTGAGTGCC CT (SEQ ID NO: 48) | |
| OsNF-YA_Effector (pHBT) | TCCCCTTGCTCCGTGGATCC ATGGAGGACACCCGAATCC TGC (SEQ ID NO: 49) | AATGTTTGAACGATCTGCAGTCA CACCTTGAGGAGGTCGACG (SEQ ID NO: 50) |

The constructs were transformed into rice plants (*Oryza sativa* cv. Dongjin) by *Agrobacterium* (LBA4404) mediated co-cultivation, as described previously (Jang, I C., et al., Molecular Breeding (1999) 5:453-461). Copy numbers of transgenic plants were determined by TaqMan Q-PCR (Thermo Fisher) using the probes specific for the bar and Tubulin genes. To analyze the copy number of the transgenic rice plants, genomic DNA was extracted from 2-week-old rice seedlings. Genomic DNA extracted from transgenic plants previously confirmed single inserted homozygous line was used as a control. The selected transgenic plants were self-fertilized, and homozygous transgenic lines were selected from T2 generations by analyzing the segregation ratio on MS media containing phosphinothricin (Duchefa). Three independent single-copy inserted homozygous plants were selected and propagated in a rice paddy field at Kyungpook National University, Gunwi (128:34E/36:15N), Korea for further propagations.

RNA Isolation and Quantitative Real-Time PCR Analysis

Total RNAs were extracted from rice leaf or root tissues using a Hybrid-R RNA purification kit (GeneAll Biotechnology) according to the manufacturer's instructions. To generate first-strand complementary DNA (cDNA), 2 μg of total RNAs were reverse-transcribed using RevertAid M-MuLV Reverse Transcriptase (Thermo Scientific). Real-time PCR analysis was performed using the 2× Real-Time PCR smart mix (SolGent) and EvaGreen (SolGent) in AriaMx real-time PCR Systems (Agilent). The PCR reactions were performed by initial denaturation at 95° C. for 10 min, followed by 40 cycles of 95° C. for 20 s, 60° C. for 20 s, and 72° C. for 30 s. Rice Ubiquitin1 (Os06g0681400) was used as an internal control for normalization. Three Technical replicates were analyzed for quantitative experiments. Primers used for qRT-PCR experiment were listed in Table 1.

Rice Protoplast Preparation and Transient Gene Expression

To determine subcellular localization of OsNF-YA5, the coding region of OsNF-YA5 was cloned into the pHBT-GFP vector, and OsNAC14 coding sequence was cloned into the pHBT-mcherry vector through BamHI and PstI restriction enzyme sites (NEB, USA) using In-fusion system (Takara, Japan). Rice seedlings (*Oryza sativa* cv. Ilmi) were grown in the dark for 10 days and transferred to the light conditions for 8 to 10 hours. Leaf sheaths of fifty rice seedlings were cut into 0.5 mm pieces using a sharp blade on a glass. Rice protoplast preparation and transient gene expression were performed as described previously (Shim, J. S. et al., Frontiers in Plant Science (2018) 9:310). After incubation at 28° C., the protoplasts were harvested by centrifugation at 300 g for 2 min. The subcellular localization of OsNF-YA5 was observed by a Leica SP8 STED laser scanning confocal microscope (Leica).

Determination of Chlorophyll Content and SPAD Measurement

The chlorophyll content in rice seedlings was analyzed as described previously (Ni, Z. et al., Nature (2009) 457:327-331). The chlorophyll content was calculated based on the absorbance at 645 and 663 nm. Three biological replicates were analyzed for quantifying chlorophyll content. The relative chlorophyll content in leaves of transgenic and non-transgenic plants grown in the paddy field was determined by a Soil Plant Analysis Development (SPAD) value measured by an SPAD-502 Plus chlorophyll meter (Konica Minolta) according to the manufacturer's instructions.

Agronomic Trait Analysis of Rice Plants Grown in a Paddy Field

To analyze the agronomic traits of the transgenic and NT rice plants, NT plants, and two independent $T_4$ homozygous transgenic lines were planted in a paddy field at the Kyungpook National University, Gunwi (128:34E/36:15N), Korea in 2020. Three separated paddy fields were used, and each filed was applied for different amount of N fertilizer (0% N, 0 g/are; 20% N, 180 g/are; 100% N, 900 g/are). While the same amount of other nutrients, including P and K, were supplied in each field. The experiment included three replicates where three different plots were planted in a randomized design. The yield components of 30 plants per line from the three different plots in each N field, were measured and analyzed.

RNA Sequencing Analysis 10-day-old GOS2::OsNF-YA5-GR plants grown on MS solid media were treated with 50 μM dexamethasone (DEX) solution containing 0.02% (w/v) Silwet L-77. For mock treatments, 0.02% Silwet L-77 was sprayed into rice plants. To minimize the effect by the treatment, plants were pre-treated with 0.02% Silwet L-77 3 hours before DEX treatment. Total RNAs were extracted from GOS2::OsNF-YA5-GR transgenic plants harvested 3 and 9 hours after DEX-treatments using Plant RNeasy mini kit (Qiagen, Germany). Two biological replicates for each time point were prepared for RNA sequencing analysis. Single-end sequences were obtained using IRGSP (v 1.0), and raw sequence reads were trimmed to remove adaptor sequences, and those with a quality lower than Q20 were removed using the Trimmomatic 0.32 software (http://www.usadellab.org/cms/?page=trimmomatic). To map the reads to reference genome, all reads were assembled with annotated genes from the Rap-DB database [http://rapdb.dna.affrc.go.jp; IRGSP (v 1.0)] using TopHat software (https://ccb.jhu.edu/software/tophat/index.shtml). After mapping reads to a reference genome, differentially expressed genes (DEG) were analyzed and validated by more than two-fold change value and independent T-test (p-value<0.1). The data set can be found at from GEO database with series accession number GSE178682 for RNA-sequencing data.

Protoplast Isolation and Transactivation Assay

The OsNF-YA5 and a series of deleted promoters of OsNRT1.1A were amplified by PCR using a high-fidelity DNA polymerase PrimeSTAR (TaKaRa). For effector constructs, OsNF-YA5 was cloned into the pHBT vector (GenBank accession number EF090408) containing the 35S promoter, and for the reporter construct, a series of deleted OsNRT1.1A promoters were cloned into the pGST6-LUC-NOS vector (GenBank accession number EF090412.1) using the In-fusion cloning system (TaKaRa). Protoplast isolation from shoots of 10-day-old rice seedlings (*O. sativa* cv. Dongjin) and PEG-mediated transformation was performed as previously described (Jung, H., et al., Plant Sci (2015) 236:304-312). Fifteen microlitres of vector solution, including 3 µg of effector, 1 µg of reporter, and 1 µg of internal control, were transfected into the isolated protoplast solution harboring up to $3.5 \times 10^6$ cells. Dual-luciferase activity was analyzed using the dual-luciferase reporter assay system (Promega, Madison, Wis.) and measured with an Infinite M200 system (Tecan Systems, CA). Three independent transfections for each sample were performed, and the relative luciferase activity was calculated as the ratio between fLUC and rLUC. 35S::rLUC construct was used as an internal control. Primer sequences are listed in Table 1.

Ammonium Uptake Assay

For ammonium uptake, $T_4$ OsNF-YA5 overexpressing, knockout transgenic plants, and WT plants were grown in a liquid culture solution for 3 weeks. The solution was changed every 3 days to ensure a consistent supply of nutrients. On the $4^{th}$ week, plant roots were washed with running water, and plants were transferred to a new tank containing Yoshida solution without N and allowed to grow for 10 more days. After 10 days of N-starvation, ammonium sulfate corresponding to three N-concentrations (0.01, 0.1, and 1 mM N) was introduced. Before sampling, roots were washed with water containing 1 mm $CaSO_4$ for 1 min to remove any ammonium present on the surface of the roots. For confirmation using different overexpression systems, three independent homozygous $T_4$ G (19, 20) R (5, 7), and KO (1,2), as well as WT plants, were subjected to the same stress as the OsNF-YA5 transgenic plants. Samples were ground in liquid nitrogen and kept in a −80° C. freezer until use. For ammonium analysis, the Berthelot reaction was followed with some modifications as described in the previous report (Redillas, M. et al., 2019).

Amino Acid Analysis

Amino acid quantification was requested to National Instrumentation Center for Environmental Management (NICEM) in Seoul National University, Korea. Analysis was done using HPLC Ultimate 3000 equipped with column VD Spher 100 C18-E (4.6 mm×150 mm, 3.5 µm/VDS, Optilab, Germany) and FL detector 1260 FLD (Agilent Technologies, Santa Clara, Calif., USA) according to the manufacturer's manual.

Example 1. Characterization of OsNF-YA5 Expression Response to Nitrogen

Figure 2A:
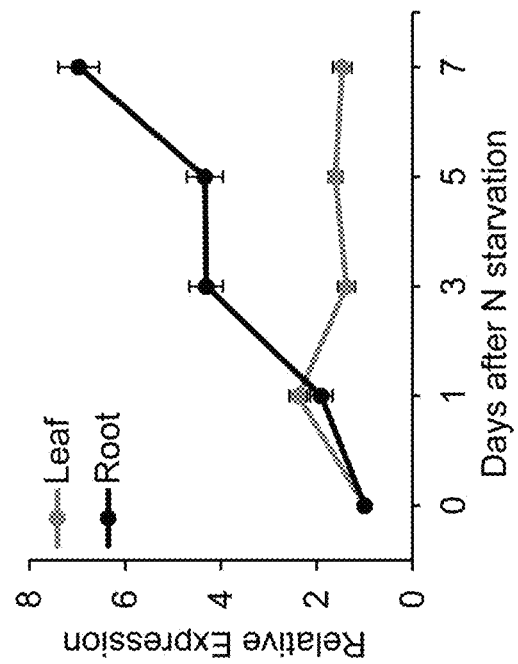
FIGS. 2a to 2d show the characterization of rice OsNF-YA5 expression. (a) Experimental scheme for N-starved sample preparation (left) and OsNF-YA5 transcription level in the leaf and root under nitrogen deficient condition with time-course (right). (b) OsNF-YA5 expression in rice grown on MS media with different N concentration. Total RNAs were extracted from roots and shoots grown on MS media containing no N source (MS-N) and MS-N supplemented with increasing concentration of potassium nitrate. MS-0 media was used as control. Leaf and root tissues were collected for qRT-PCR analysis. Transcript levels were normalized to OsUbi1 expression. Values are the means±SD of three biological samples (n=3) (c) Expression of OsNF-YA5 across the developmental stages of rice. Triangle indicates the value used for normalization. D, dark; L, light; d, day after germination; m, month after germination; BH, before heading; AH, after heading. (d) Subcellular localization of OsNF-YA5 in nucleus. Rice protoplasts were transiently co-transformed with 35S:OsNF-YA5-GFP and a nuclear localization marker 35S:OsNAC14-mCherry (Shim et al., 2018). Fluorescence was observed under a confocal microscope. White bar=5 μm.
Figure 2A:
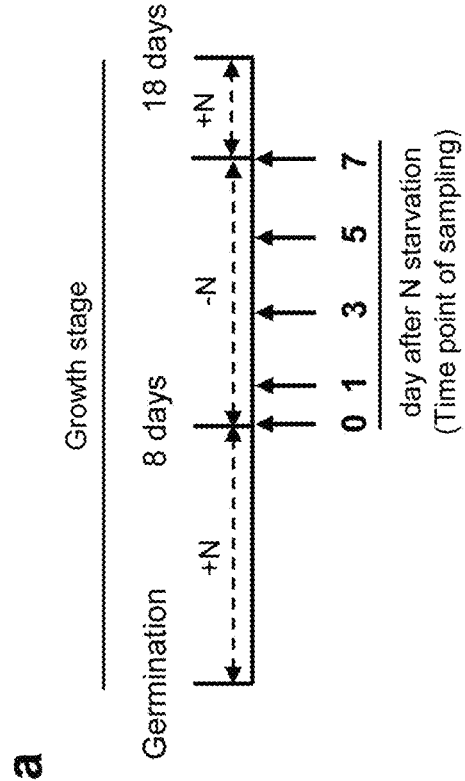
Figure 2B:
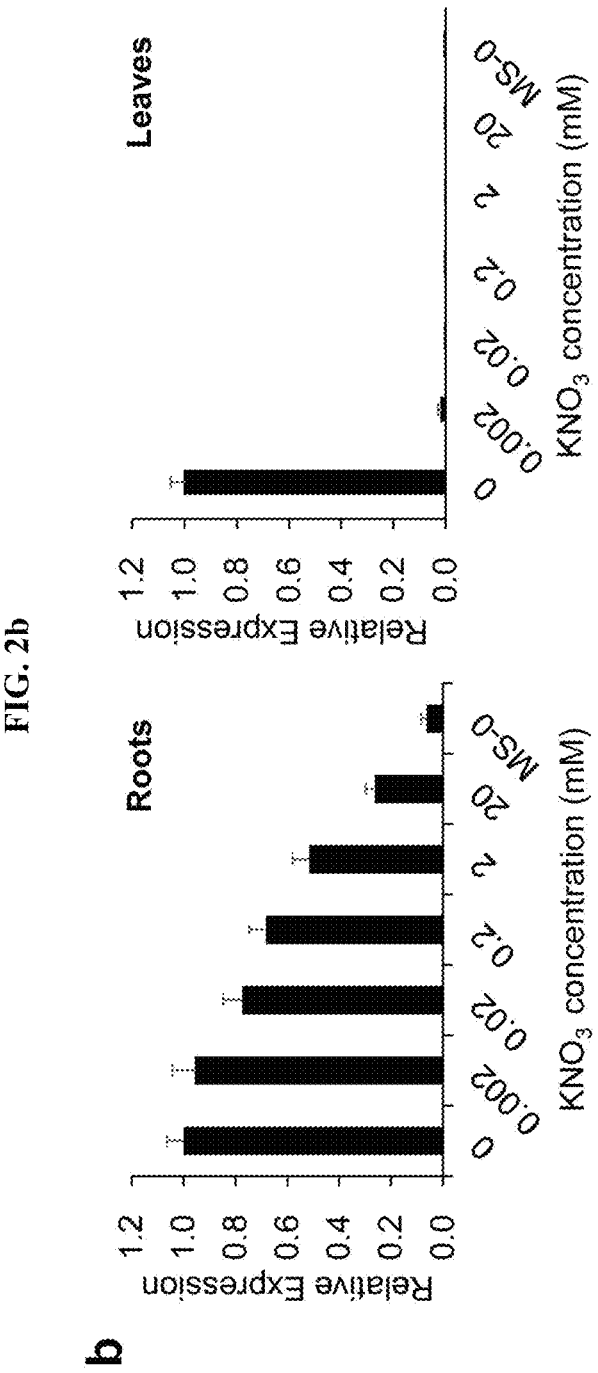

Previously, we investigated the rice transcriptome in root and leaf tissue under N starvation condition. In this experiment, NF-YA5 expression significantly correlated with N nutrient condition (a of FIG. 1). To confirm the N dependency of NF-YA5 expression, rice (cultivar Dongjin) was grown in normal nutrient liquid media for eight days, then moved to N deficient media and grown for seven days. Total RNA was prepared from root and leaf at different time points (0, 1, 3, 5, and 7 days) (FIG. 2a; left panel). The transcription level of OsNF-YA5 was gradually increased in the root after exposure to N deficient condition, however, not significantly changed in the leaf tissue (FIG. 2a; right panel). To investigate the N dependency of OsNF-YA5 expression further, we checked the transcription level of OsNF-YA5 in the plant grown on the media harboring different N nutrient concentrations ($KNO_3$). Results clearly showed that OsNF-YA5 expression was dependent on N concentration in the root (FIG. 2b). OsNF-YA5 expression was repressed in N-sufficient condition, whereas OsNF-YA5 expression was increased in N deficient condition. These results suggested that the OsNF-YA5 transcription level was tightly regulated in the root by N nutrition status.

Figure 2C:
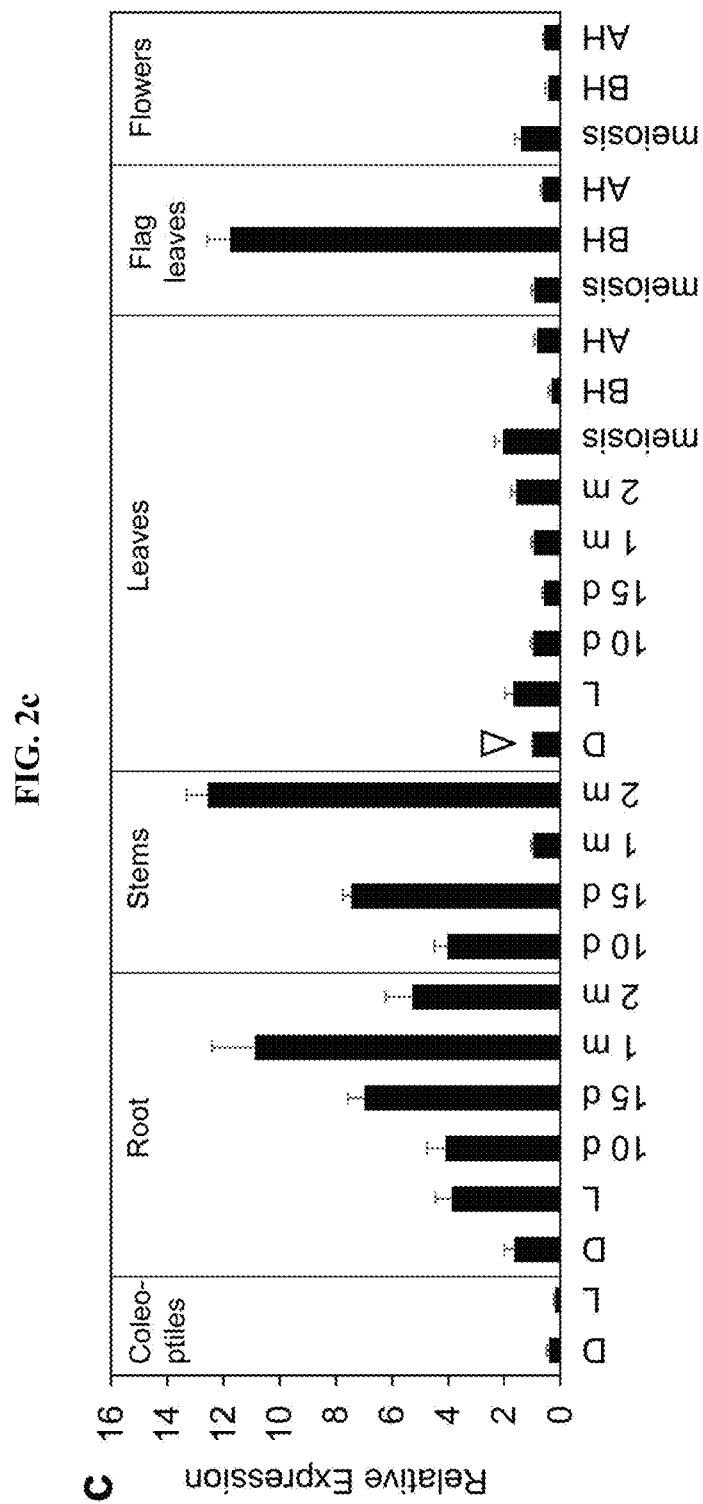
Figure 2D:
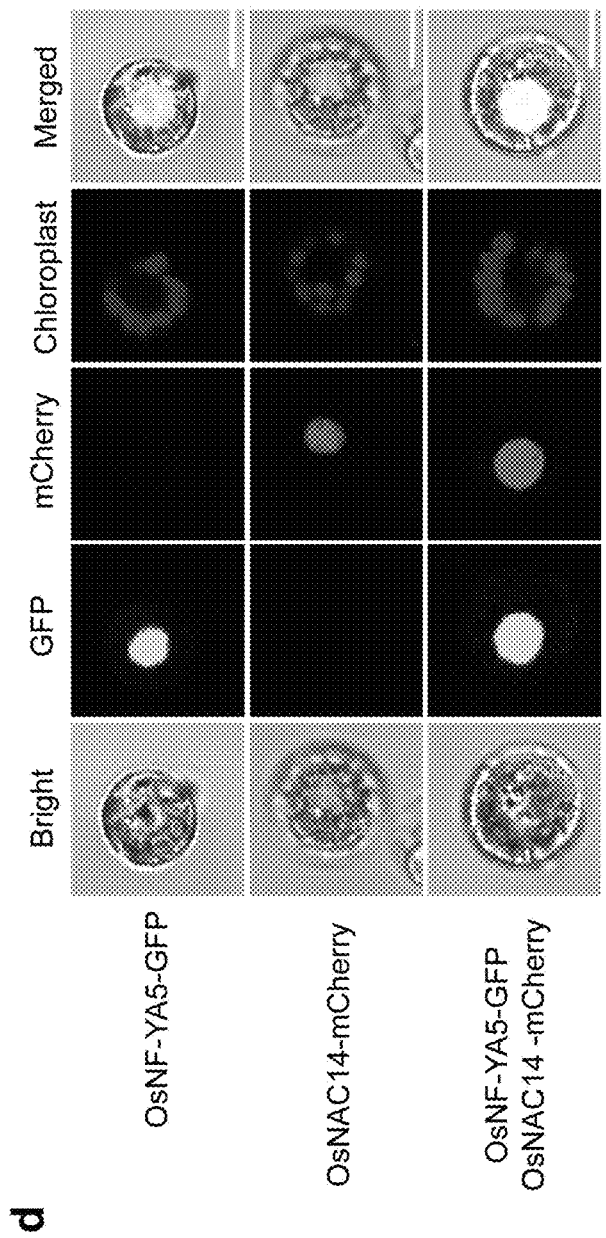

We also analyzed the expression profile of OsNF-YA5 at various developmental stages of coleoptiles, roots, stems, leaves, flag leaves, and flowers. qRT-PCR data showed that OsNF-YA5 transcripts were detected at all developmental stages. OsNF-YA5 was highly expressed in two different tissues, roots and stems. In contrast, the expression level was relatively low in the leaf and flower tissue (FIG. 2c). To verify the subcellular localization of OsNF-YA5, we generated a construct to express translationally fused OsNF-YA5 and green fluorescent protein (GFP) (OsNF-YA5-GFP) driven by the CaMV 35S promoter and transiently expressed in rice protoplasts together with OsNAC14-mCherry as a positive control for nuclear localization. The fluorescence signals from both GFP and mCherry were co-localized in the nuclear region, confirming that OsNF-YA5 is a nuclear-localized protein (FIG. 2d).

Figure 3:
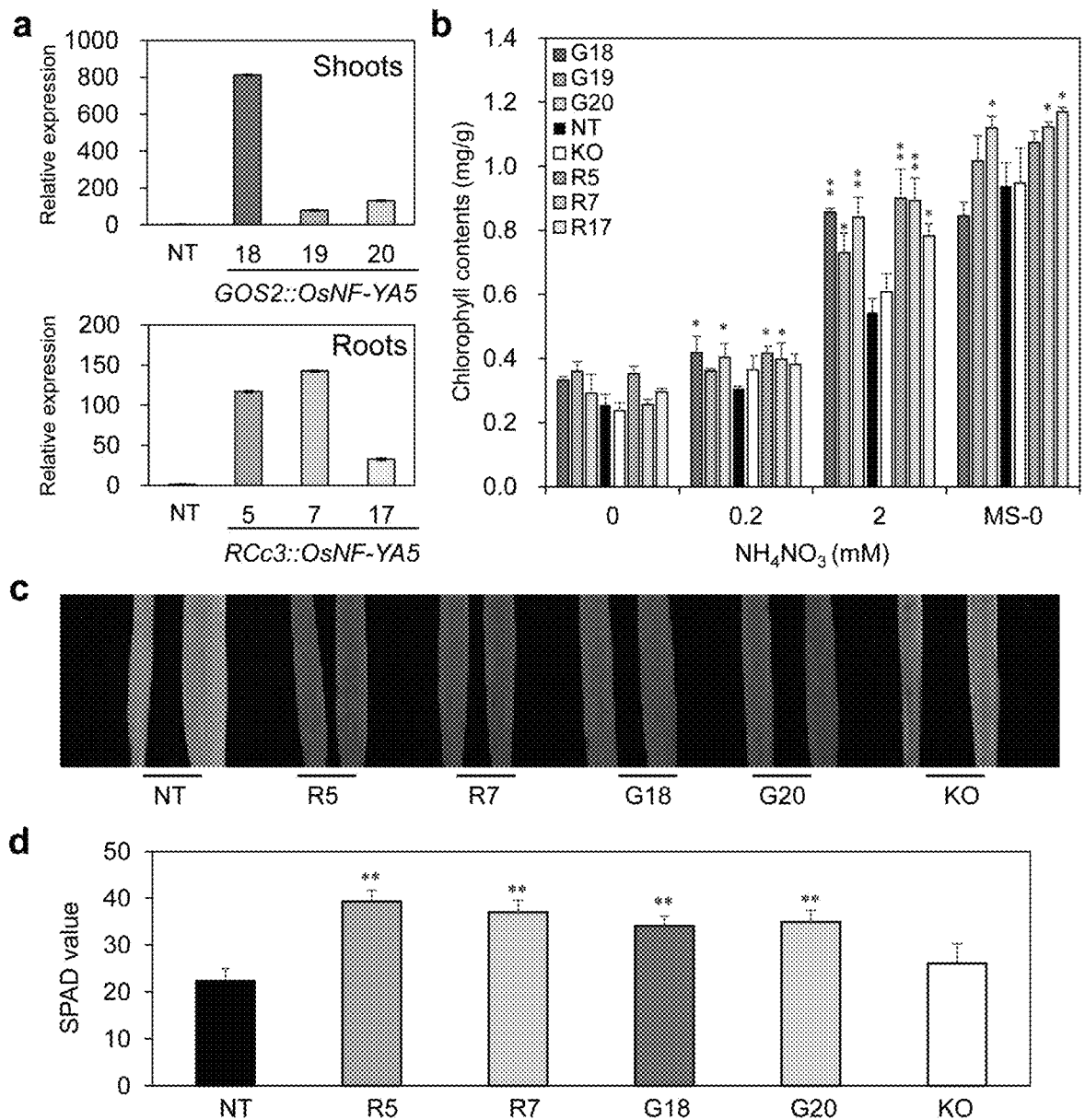
FIG. 3 shows the analysis of chlorophyll contents in OsNF-YA5 transgenic plants. (a) Expression levels of OsNF-YA5 overexpressing transgenic plants (left panels). Total RNAs were extracted from shoots of ten-day-old whole-body overexpression plants (G, GOS2::OsNF-YA5), roots of root-specific overexpression plants (R, RCc3:: OsNF-YA5), osnfya5 mutant (KO), and NT plants. (b) Measurement of chlorophyll contents in the plants grown on MS media with different concentration of nitrogen source. Plants were grown in a dark chamber for 3 days and transferred to light for 4 more days. Leaves were collected for measuring total chlorophyll contents. (c) Leaf phenotype of 24-week-old transgenic and non-transgenic plants grown in paddy field, and (d) SPAD value measurement. The data represent the means±SD of three biological replicates (n=3). Asterisks indicate a statistically significant difference compared with NT. *P<0.05, **P<0.01; two-tailed t-test.
Figure 4:
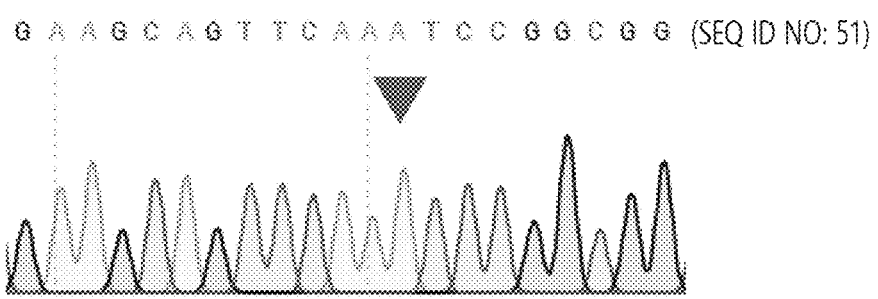
FIG. 4 shows the generating knockout mutant of OsNF-YA5 by CRISPR-Cas9 system. (a) Comparison of genomic DNA sequence between NT and osnfya5 mutant. (b) ORF analysis of NT and osnfya5 mutant. Triangle showed mutated site of OsNF-YA5 locus. Number indicates the amino acid (AA) number from first Met(1).
Figure 4:
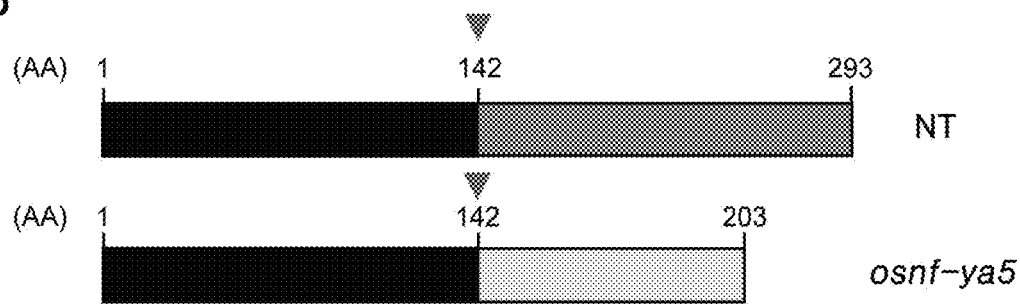

Example 2. Overexpression of OsNF-YA5 Increases Chlorophyll Contents and Delays Leaf Senescence To understand the function of OsNF-YA5 in plant N-response, we generated transgenic plants expressing OsNF-YA5 under the control of constitutive GOS2 promoter (GOS2::OsNF-YA5, G) or root-specific RCc3 promoter (RCc3::OsNF-YA5, R). The qRT-PCR analysis confirmed that OsNF-YA5 is overexpressed in the transgenic plants compared to non-transgenic (NT) plants (a of FIG. 3). In addition, the knockout mutant of OsNF-YA5 (KO) was generated by CRISPR/Cas9-mediated mutagenesis (FIG. 4). It has been well characterized that chlorophyll is a major sink of nitrogen in vegetative stages, and there exists a positive correlation between chlorophyll content and internal N content. Thus, we analyzed chlorophyll content in NT, G, R, and KO seedlings grown with various concentrations of N source. Both G and R transgenic plants showed significantly higher chlorophyll content than NT plants in low N source conditions. However, the chlorophyll content of KO plants showed a similar chlorophyll content with NT (b of FIG. 3). These results indicate that OsNF-YA5 plays a positive regulator in the chlorophyll contents, which reflects internal N concentration.

Another featured phenotype of plant nitrogen response is leaf senescence. Generally, leaf senescence is accelerated in N deficient condition, while is delayed in N sufficient condition. We checked the visual phenotype of leaves at the ripening stage grown in the paddy field. G and R overexpressing transgenic plants showed significantly delayed leaf senescence compared to NT (c of FIG. 3). Besides, SPAD values of overexpressing plants were higher than those of NT. In contrast, KO has no significant changes compared to NT (d of FIG. 3). It suggested that overexpression of OsNF-YA5 delayed leaf senescence at the ripening stage. Taken together, all the results strongly support the idea that OsNF-YA5 improves the internal nitrogen content of the plant.

Example 3. OsNF-YA Improves Grain Yield Under N Deficient Condition

Figure 5:
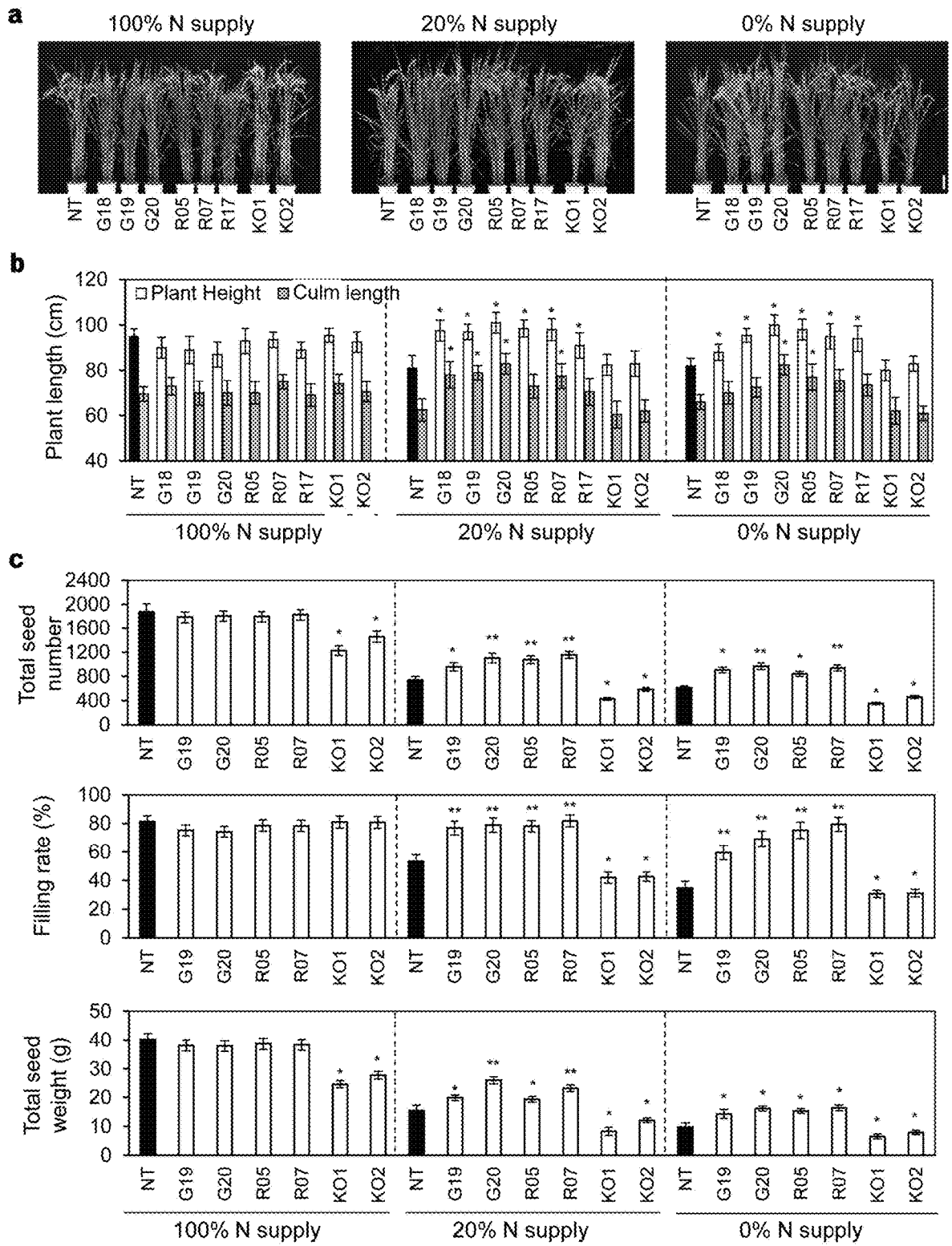
FIG. 5 shows the agronomic traits of OsNF-YA5 transgenic plants grown under modified N supply conditions. Morphology (a) and plant height (b) of transgenic lines grown on the paddy field with different amount of N fertilizer application for 5 months. (c) Measurement of agronomic traits, total seed number, filling rate, and total seed weight of transgenic plants grown on the field (in 2020). Applied amount of N fertilizer was 0 kg/are (0% N), 180 g/are (20% N), and 900 g/are (100% N). G18-20, GOS2:NF-YA5 #18-20; R5, 7, 17, RCc3:NF-YA5 #5, 7, 17; KO1-2, osnf-ya5 #1, #2. The data represent the means±SD of three biological replicates (n=3). Asterisks indicate a statistically significant difference compared with NT as analyzed by one-way ANOVA followed by t-test. *P<0.05, **P<0.01; two-tailed t-test.

We evaluated plant phenotypes and agronomic traits of OsNF-YA5 transgenic plants in the field condition. Three independent T4 homozygous lines of G (G18, G19, and G20) and R (R5, R7, and R17) plants, together with NT controls, were transplanted to a paddy field and grown to maturity with a modified amount of N fertilizer application (field in 2020). In normal N conditions, plant height and culm length were similar between NT and transgenic plants. In comparison, plant height and culm length of overexpressing transgenic lines were higher than those of NT under N starvation conditions (20% and 0% N) (a and b of FIG. 5). We analyzed the three yield parameters, total seed number, filling rate, and total seed weight of two independent lines. The yield parameters were scored for 30 plants per transgenic line from three replicates. All the yield parameters were similar among overexpressing transgenic plants and NT; however, total seed number and weight of KO plants were decreased by 22~34% and 31~39% in normal N condition (100% N) (c of FIG. 5). On the other hand, the yield parameters significantly enhanced overexpressing transgenic lines while decreasing in KO plants compared to NT plants (c of FIG. 5). The total seed number of G and R transgenic plants was increased by 29~57% and 37~64%, respectively, whereas KO plants showed decreased seed number by 21~43% in N deficient condition (0% and 20% N supply). The filing rate of G and R transgenic plants was not significantly affected by N deficiency, and KO plants showed 10~20% less filing rate compared to NT plants. Also, G and R transgenic plants showed 28~67% and 25~67% increase of total seed weight, respectively, whereas KO plants showed decreased total seed weight by 19%~46% in N deficient condition.

Example 4. Identification of Downstream Genes Regulated By OsNF-YA5

Figure 6:
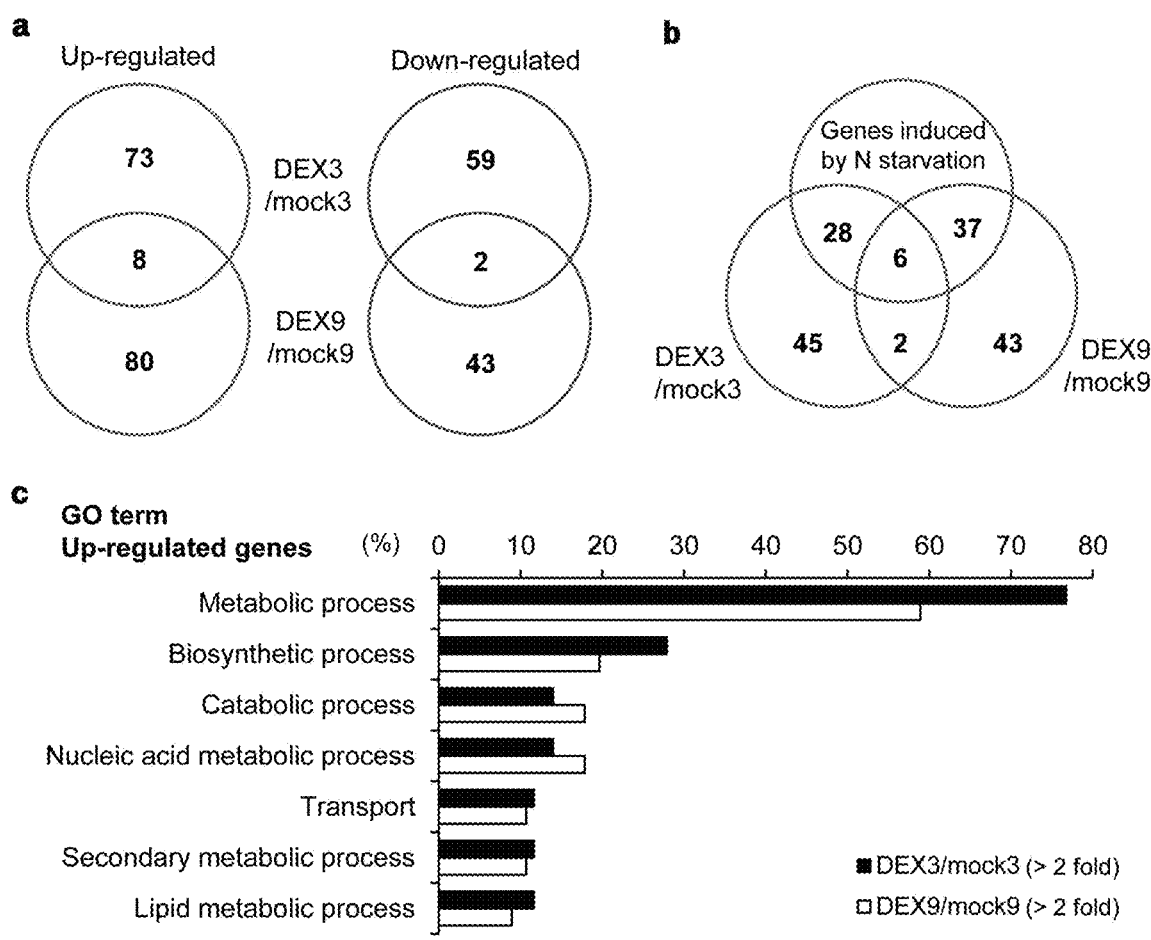
FIG. 6 shows the transcriptome analysis by RNA-seq after DEX treatment. RNA-seq analysis was performed with 4-week-old GOS::OsNF-YA5-GR transgenic plants after DEX treatment (3 h and 9 h). Then genes that showed over 2 fold change in expression compared to mock treatment samples were isolated. (a) The Venn diagram showed the number of up-regulated and down-regulated genes in 3 h and 9 h DEX treated samples. (b) Venn diagram showed the number of overlapped genes up-regulated by DEX treatment or N starvation condition. (c) Gene ontology (GO) analysis of up-regulated genes by DEX treatment. The percentage value of classified gene number among total up-regulated gene number was shown.

To understand how OsNF-YA5 improves the N use efficiency, we attempted to identify genes involved in the OsNF-YA5-mediated transcriptional network. We generated transgenic plants expressing OsNF-YA5-glucocorticoid receptor (GR) fusion protein under the control of constitutive GOS2 promoter (OsNF-YA5-GR$^{OX}$) to use DEX (dexamethasone) inducible system. After OsNF-YA5-GR$^{OX}$ transgenic plants were treated with mock or DEX for 3 hr or 9 hr, we investigated the change of transcriptome using RNA sequencing. At least 2-fold change was used as the cutoff value to identify differentially expressed genes (DEGs), and a student's t-test was applied to discard data for genes that were not statically relevant (P<0.1). RNA sequencing analysis revealed that 81 (3 hr DEX treatment) and 88 (9 hr DEX treatment) genes were up-regulated. In comparison, 61 (3 hr DEX treatment) and 45 (9 hr DEX treatment) genes were down-regulated in OsNF-YA5-GR$^{OX}$ transgenic plants by DEX treatment compared to mock treatment (a of FIG. 6). Among 145 up-regulated genes, 71 genes (49%) were also up-regulated in N starvation conditions (b of FIG. 6). GO term analysis of up-regulated genes revealed that 59~76% of genes were involved in the metabolic process, and 10~12% were transporter (c of FIG. 6). These results suggested that OsNF-YA5 regulated the genes involved in the metabolic process.

Figure 7:
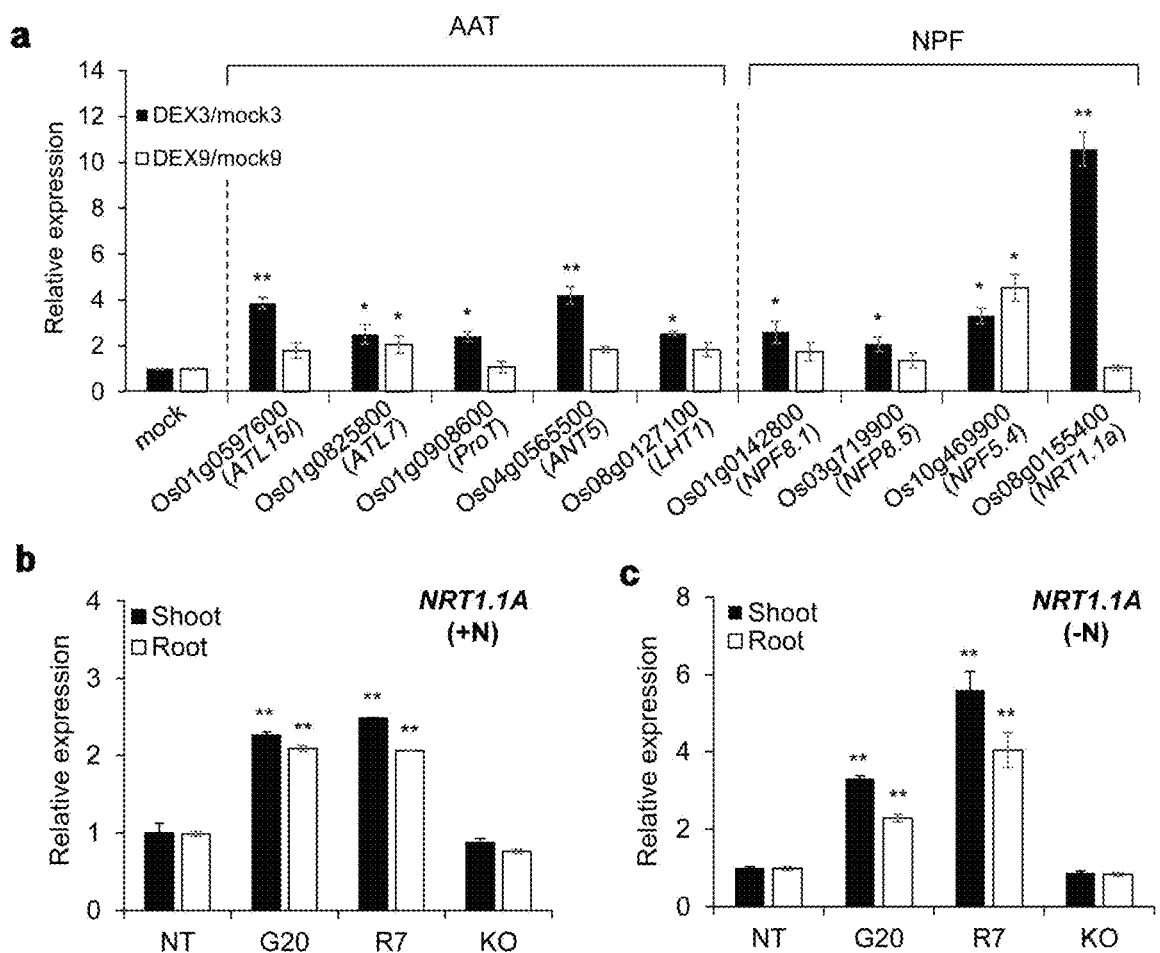
FIG. 7 shows the isolation of NF-YA5 target genes using dexamethasone (DEX)-inducible system. RNA sequencing analysis were performed using GOS2:NF-YA5-GR transgenic plants after mock and DEX treatment (3 h and 9 h) and screened the putative target genes (fold change≥2) (a) Expression level of screened amino acid transporters (AAT) and nitrate/peptide transporter family (NPF) genes in GOS2:NF-YA5-GR transgenic plants after DEX treatment. (b) Transcript level of NRT1.1a in OsNF-YA5 transgenic lines under nitrogen sufficient condition. (c) Transcript level of NRT1.1a in OsNF-YA5 transgenic lines under nitrogen deficient condition. G20, GOS2:NF-YA5 #20; R7, RCc3:NF-YA5 #7; KO, osnf-ya5. Transcript levels were normalized to OsUbi 1 expression. The data represent the means±SD of three biological replicates (n=3). Asterisks indicate a statistically significant difference compared with mock (a) or NT (b). *$P<0.05$, **$P<0.01$; two-tailed t-test.

We isolated the up-regulated genes of the amino acid transporter (AAT) and nitrate/peptide transporter family (NPF) based on RNA-seq data. We confirmed it by qPCR analysis after DEX treatment. 5 AAT genes and 4 NPF genes were up-regulated over two-fold after DEX treatment (a of FIG. 7). Interestingly, the transcript level of OsNRT1.1A was significantly induced, which suggested that OsNRT1.1A was a strong candidate among the putative OsNF-YA5 targets. To check the expression level of OsNRT1.1A in OsNF-YA5 transgenic plants, we performed the qPCR analysis with leaf and root tissues under N sufficient (+N) and deficient (−N) conditions. The results showed that OsNRT1.1A expression was enhanced in leaf and root tissue of overexpressing plants under both +N or −N conditions. In contrast, The OsNRT1.1A expression level in the KO plant was similar to the NT plant (b of FIG. 7). Therefore, OsNF-YA5 enhances OsNRT1.1A transcription level in rice.

Figure 8:
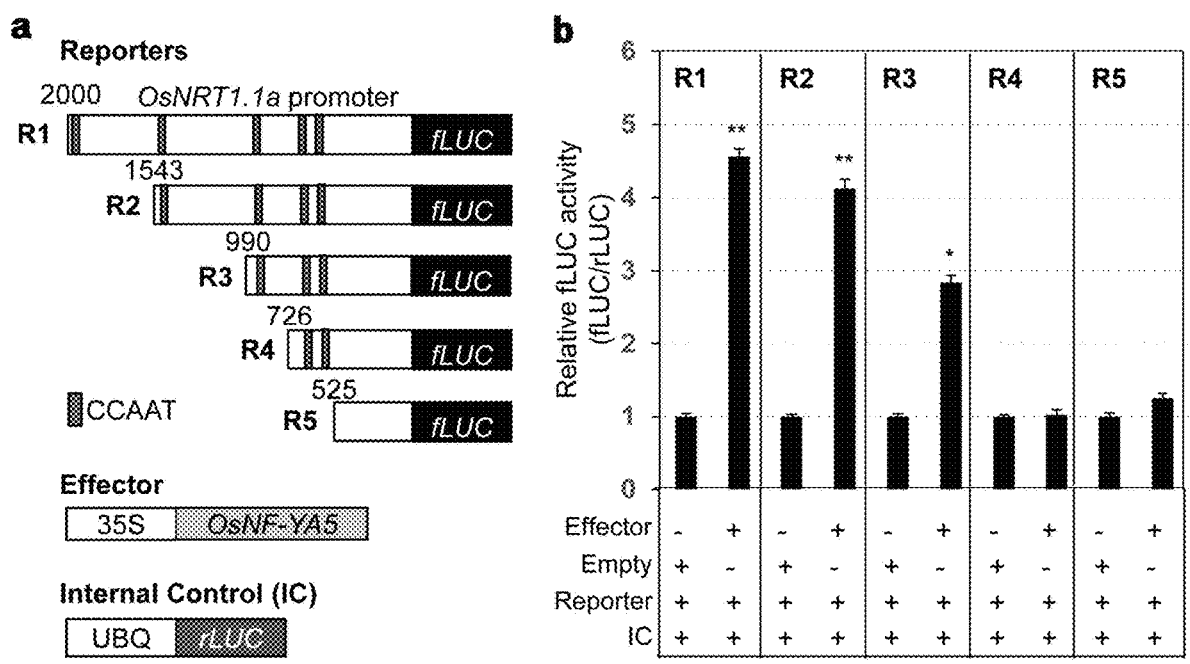
FIG. 8 shows the transactivation assay using dual luciferase reporter system. Transient protoplast expression assay using a dual-luciferase reporter system. (A) Schematic diagram of five reporters, internal control and effector constructs. Reporter constructs fused with Series of the deleted OsNRT1.1a promoter (left). (B) Relative fLUC (fLUC/rLUC) activity in rice protoplast after transformation with different combination of reporter and effector. The data represent the means±SD of three biological replicates (n=3). Asterisks indicate a statistically significant difference compared with NT. *$P<0.05$, **$P<0.01$; two-tailed t-test.

Example 5. OsNF-YA5 Directly Regulates OsNRT1.1A Expression, a Key Nitrogen Sensor in Rice To identify whether OsNRT1.1A is the direct target of OsNF-YA5 or not, we carried out a transactivation assay in protoplast using a dual-luciferase reporter system. We designed five deleted series of OsNRT1.1A promoter considering the position of CCAAT element, known as NF-YA binding element, and fused each of them to fLUC (firefly luciferase). Therefore, five reporter constructs (R1-R5) and CaMV35S:rLUC (renilla luciferase) were used as reporters and an internal control, respectively (a of FIG. 8). Effector plasmid, CaMC35:OsNF-YA5, was transiently co-expressed in rice protoplasts together with each reporter and internal control, as indicated (b of FIG. 8). OsNF-YA5 effectively activated the expression of R1, R2, and R3 reporters, while did not activate R4 and R5 reporters (b of FIG. 8). These results supported that OsNF-YA5 directly activated the expression of OsNRT1.1A and CCAAT element near 1 kbp upstream of OsNRT1.1A promoter was critical for activation by OsNF-YA5.

Figure 9:
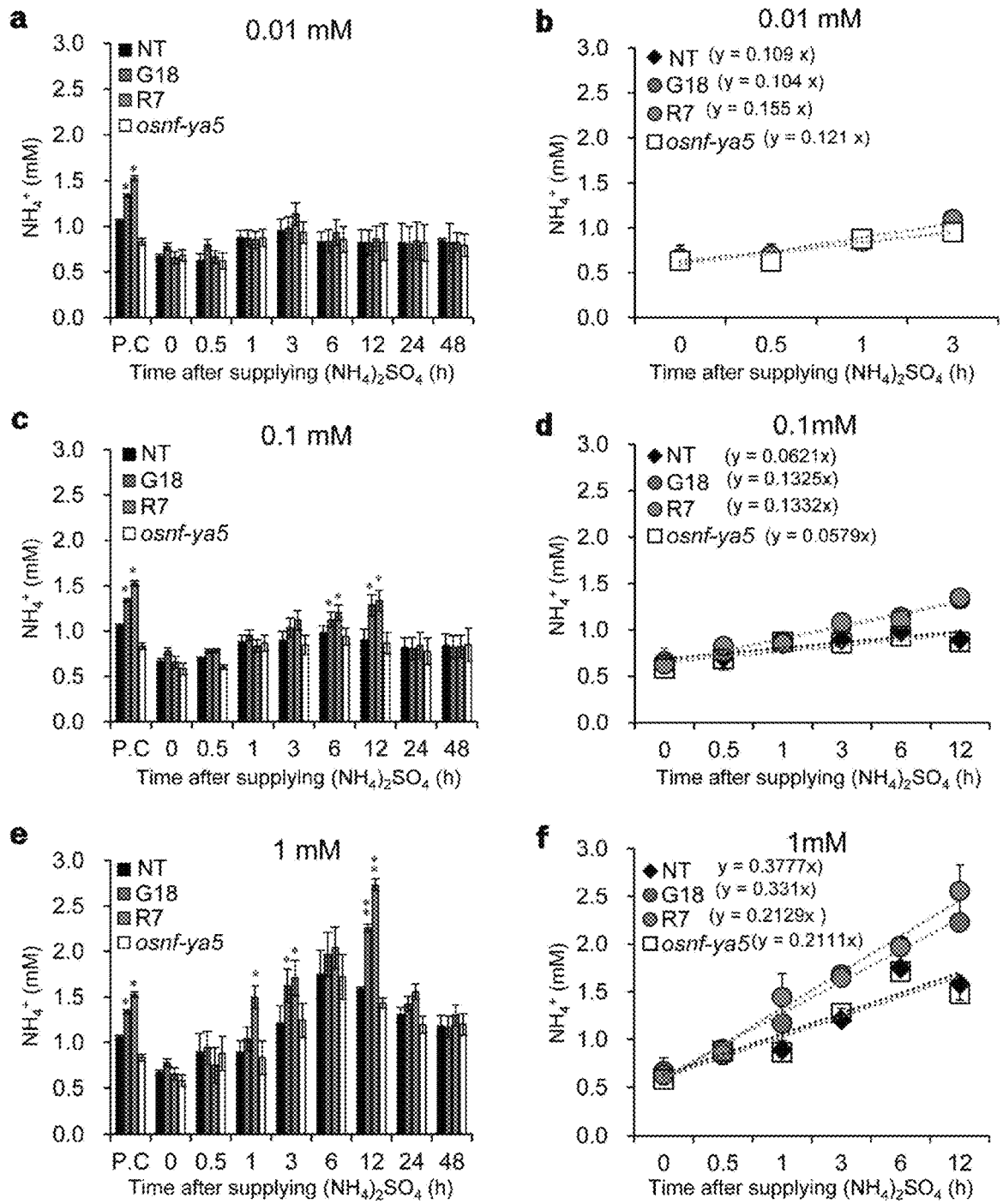
FIG. 9 shows the time-course assessment of ammonium content in roots of OsNF-YA5 transgenic rice plants. Plants were initially grown in Yoshida solution containing 1 mM N ($(NH_4)_2SO_4$) for 21 days and subjected to 10 days of N-starvation by omitting $(NH_4)_2SO_4$ in the solution. Three N-concentrations (0.01, 0.1 and 1 mM N) were then supplied and measured the ammonium content in roots. Concentration of ammonium after resupplying with (a) 0.01, (c) 0.1 and (e) 1 mM concentrations of N, respectively. Slope of ammonium accumulation in roots from the start of feeding up to the peak of accumulation when fed (b) 0.01, (d) 0.1 and (f) 1 mm N, respectively. PC: positive control; plants grown in normal N condition. NT, non-transgenic; R7, RCc3: OsNF-YA5; G18, GOS23:OsNF-YA5; KO, osnfya5 mutant. Values are the means±SD of three biological samples (n=3) and three technical repeats. Asterisks indicate a statistically significant difference compared with NT. *$P<0.05$, **$P<0.01$; two-tailed t-test.

Example 6. Ammonium Uptake Rate is Elevated in Roots of OsNF-YA5 Overexpressing Plants The previous report showed that OsNRT1.1A was involved in transporting both ammonia and nitrate in rice. We investigated the N uptake in OsNF-YA5 transgenic plants because OsNRT1.1A expression was induced in OsNF-YA5 overexpressing plants. We measured the ammonium in the roots of the plants that were normally fed N, or resupplied following 10 days N starvation. Overexpressing plants, G and R lines, grown in normal N condition showed higher ammonium contents in the root than NT plants (FIG. 9). After 10 days N starvation, ammonium content was around half in NT and transgenic plants compared to those grown in normal N condition. Moreover, there was no difference in ammonium contents among NT and transgenic plants after N starvation. During N replenishment, three N concentrations were used, 0.01, 0.1, and 1 mM N to determine whether OsNF-YA5 transgenic plants had altered N uptake compared to NT plants. At the 0.01 mM N condition, ammonium contents among NT and transgenic plants showed similar levels during 48 hours of N replenishment.

Overexpressing lines, G and R, showed higher ammonium content during 3 to 12 hours of 0.1 mM N replenishment than NT plants. Differences of ammonium contents among NT and overexpressing plants become more significant at 1 mM N replenishment condition. Ammonium content in G and R was higher by 30% and 45% compared to that of NT plants after 12 hours N replenishment. However, the ammonium content of KO plants showed similar to NT at all conditions. Taken together, results supported that OsNF-YA5 plays a positive role in N uptake and improves N uptake efficiency.

Figure 10:
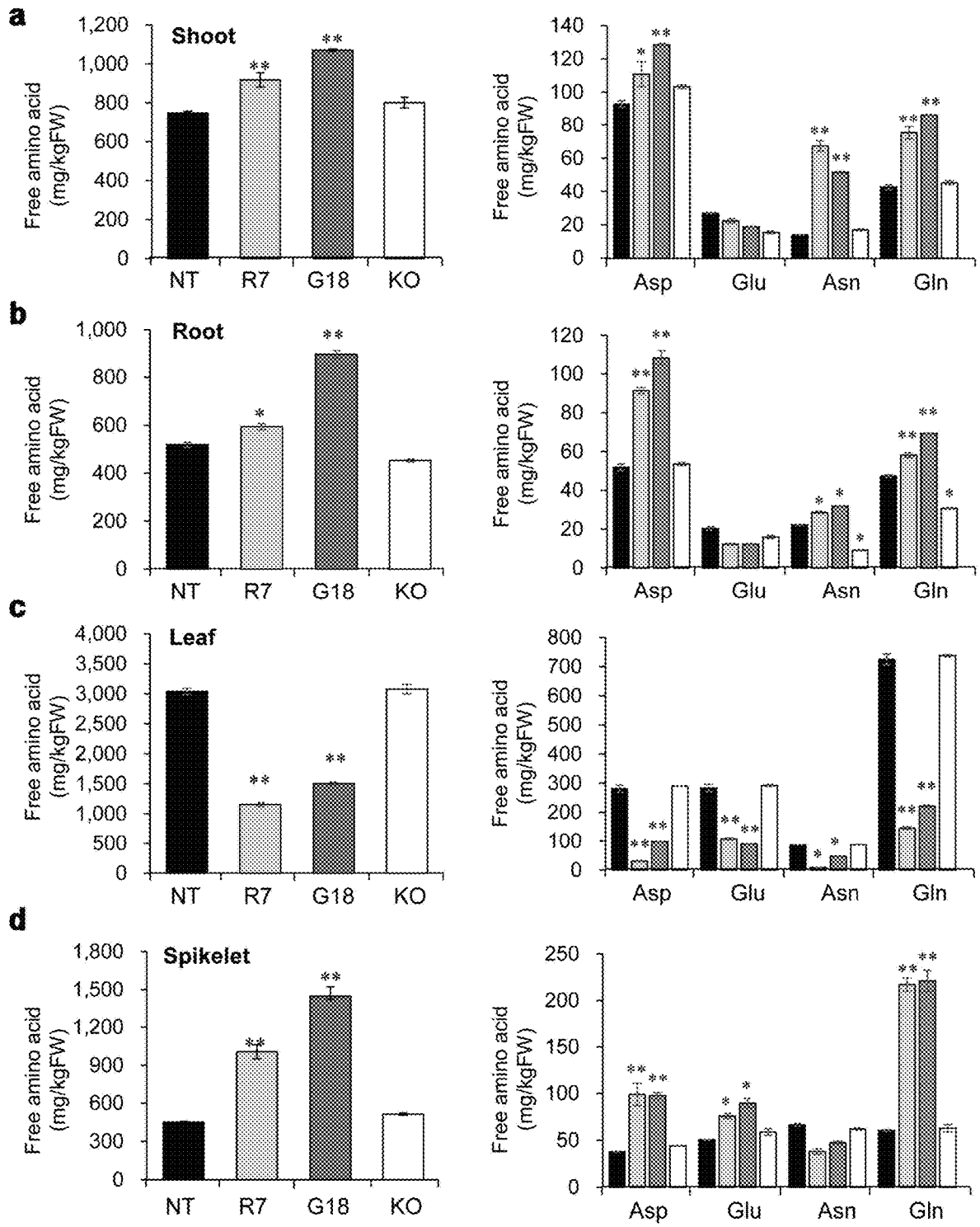
FIG. 10 shows the amino acid analysis of OsNF-YA5 transgenic plants. OsNF-YA5 transgenic seedlings were grown in N deficient liquid media for 2 weeks and analyzed total free amino acid content (left) and four amino acids involved in nitrogen assimilation (right) in the (a) shoot or (b) root of each transgenic seedlings. OsNF-YA5 transgenic plants were grown in paddy field until ripening stage and analyzed total free amino acid content (left) and four amino acids involved in nitrogen assimilation (right) in the (c) leaf or (d) spikelet of each transgenic plant. NT, nontransgenic; R7, RCc3:OsNF-YA5; G18, GOS23:OsNF-YA5; KO, osnf-ya5 mutant. The data represent the means±SD of three biological replicates (n=3). Asterisks indicate a statistically significant difference compared with NT. *$P<0.05$, **$P<0.01$; two-tailed t-test.

Example 7. Free Amino Acids Content is Improved in OsNF-YA5 Overexpressing Plants Amino acid (AA) is one of the most abundant nitrogen species transport tissues in the plant. Besides nitrogen uptake, assimilation and mobilization are also essential components in plant nitrogen use efficiency. To address the potential function of OsNF-YA5 in assimilation and allocation of aa in plants, we analyzed free AA content at different development stages and N conditions. First, we checked the free AA contents in the vegetative stage seedlings (2-week-old) under N deficient conditions. Compared to NT plants, overexpressing (G and R) transgenic plants showed a higher accumulation of free AAs in both shoot and root tissues (a and b of FIG. 10). Moreover, glutamine (Gln) and asparagine (Asn), central N assimilated form, accumulated more in G and R plants than NT plants. These results suggested that OsNF-YA5 also play an important role in improving AA accumulation under N deficient condition.

N relocation from source to sink is a vital part of improving crop nitrogen use efficiency and yield. Therefore, we analyzed the AA content in the source (leaf) and sink (spikelet) tissues at the ripening stage. Compared to NT plants, OsNF-YA5$^{OX}$ and OsNF-YA5$^{ROX}$ transgenic plants showed lower accumulation of free AAs in source tissue, leaves (c and d of FIG. 10). Interestingly, both OsNF-YA5$^{OX}$ and OsNF-YA5$^{ROX}$ transgenic plants showed a significantly higher accumulation of free AAs in grains than NT plants. Free AAs level in KO mutant plants was similar to that of NT plants. Further AA profiling revealed that level of several AAs, such as aspartic acid (Asp), asparagine (Asn), glutamic acid (Glu), and glutamine (Gln), were reduced in leaves of both OsNF-YA5$^{OX}$ and OsNF-YA5$^{ROX}$ transgenic plants. On the contrary, Asp, Glu, and Gln were higher in spikelets of OsNF-YA5 overexpressing transgenic plants than NT plants. Especially, glutamine level was significantly lower in source tissues (leaves) but higher in sink tissues (grains) in both G and R transgenic plants than NT plants. Collectively, these data suggest that OsNF-YA5 regulates the accumulation and allocation of free AAs according to developmental stage.

A sequence listing electronically submitted with the present application on Aug. 3, 2021 as an ASCII text file named 20210803_Q57621GR09_TU_SEQ, created on Aug. 2, 2021 and having a size of 13,000 bytes, is incorporated herein by reference in its entirety.

What is claimed is:

1. A method for producing a transformed plant with increased nitrogen use efficiency compared to a non-transgenic plant, the method comprising:
   transforming a plant cell with a recombinant vector which includes the gene encoding the *Oryza sativa* Nuclear Factor Y subunit A5 (OsNF-YA5) protein of the amino acid sequence of SEQ ID NO: 2; and
   regenerating a plant from the transformed plant cell.

2. A transformed plant produced by the method according to claim 1.

3. A transformed seed of the plant according to claim 2, wherein the seed comprises the gene encoding the OsNF-YA5 protein.

* * * * *